United States Patent
Nirogi et al.

(10) Patent No.: US 9,018,231 B2
(45) Date of Patent: *Apr. 28, 2015

(54) SULFONE COMPOUNDS AS 5-HT6 RECEPTOR LIGANDS

(75) Inventors: Ramakrishna Nirogi, Hyderabad (IN); Anil Karbhari Shinde, Hyderabad (IN); Rama Sastri Kambhampati, Hyderabad (IN); Rajesh Kumar Badange, Hyderabad (IN); Veena Reballi, Hyderabad (IN); Anil Kashinath Chindhe, Hyderabad (IN); Rambabu Namala, Hyderabad (IN); Mohamad Sadik Abdulhamid Mulla, Hyderabad (IN); Ishtiyaque Ahmad, Hyderabad (IN); Renny Abraham, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 15 days.

This patent is subject to a terminal disclaimer.

(21) Appl. No.: 13/520,136

(22) PCT Filed: Mar. 24, 2010

(86) PCT No.: PCT/IN2010/000176
§ 371 (c)(1),
(2), (4) Date: Aug. 21, 2012

(87) PCT Pub. No.: WO2011/083487
PCT Pub. Date: Jul. 14, 2011

(65) Prior Publication Data
US 2013/0005709 A1   Jan. 3, 2013

(51) Int. Cl.
C07D 401/12    (2006.01)
A61K 31/4468   (2006.01)
A61P 25/18     (2006.01)
A61P 25/28     (2006.01)
C07D 211/58    (2006.01)
C07D 401/14    (2006.01)
A61K 31/4709   (2006.01)
A61K 31/4725   (2006.01)

(52) U.S. Cl.
CPC ............ C07D 211/58 (2013.01); C07D 401/12 (2013.01); C07D 401/14 (2013.01); A61K 31/4468 (2013.01); A61K 31/4709 (2013.01); A61K 31/4725 (2013.01)

(58) Field of Classification Search
CPC .................... A61K 31/4468; C07D 401/12
USPC ............ 514/415, 323, 329, 418; 546/201; 548/504
See application file for complete search history.

(56) References Cited

U.S. PATENT DOCUMENTS 7,998,981 B2 *  8/2011  Ramakrishna et al. ....... 514/323

FOREIGN PATENT DOCUMENTS

| WO | 2007020653 A1 | 2/2007 | |
| WO | WO2007/020652 | * 2/2007 | ........... C07D 401/12 |
| WO | 2007138611 A1 | 12/2007 | |

OTHER PUBLICATIONS

European Patent Office/International Search Authority; International Search Report, PCT International Patent Application No. PCT/IN2010/000176, May 3, 2011, Netherlands.
Ploemen et al., "Use of physicochemical calculation of pKa and CLogP to predict phospholipidosis-inducing potential" Exp Toxic Pathol 55:347-55 (2004).

* cited by examiner

*Primary Examiner* — Sreeni Padmanabhan
*Assistant Examiner* — Irina Neagu
(74) *Attorney, Agent, or Firm* — Iphorgan Ltd.

(57) ABSTRACT

The present invention relates to novel sulfone compounds as 5-HT$_6$ receptor ligands of the formula (I), and their derivatives, prodrugs, tautomers, stereoisomers, polymorphs, solvates, hydrates, metabolites, N-oxides, pharmaceutically acceptable salts and compositions containing them.

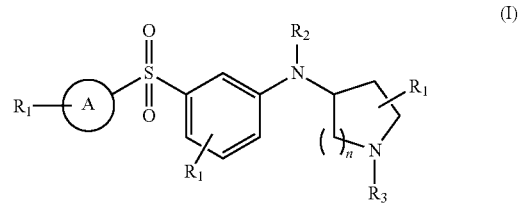

The present invention also relates to a process for the preparation of above said novel compounds, and their derivatives, prodrugs, tautomers, stereoisomers, polymorphs, solvates, hydrates, metabolites, N-oxides, pharmaceutically acceptable salts and compositions containing them.
These compounds are useful in the treatment/prevention of various disorders that are related to 5-HT$_6$ receptor functions.

12 Claims, No Drawings

SULFONE COMPOUNDS AS 5-HT6 RECEPTOR LIGANDS

CROSS-REFERENCE TO RELATED APPLICATIONS

This application is a National Stage entry of International Application No. PCT/IN2010/000176, filed on Mar. 24, 2010, which in turn claims priority to Indian Patent Application No. 18/CHE/2010, filed Jan. 5, 2010, the contents of which are both hereby incorporated by reference.

FIELD OF INVENTION

The present invention relates to novel sulfone compounds as 5-$HT_6$ receptor ligands of the formula (I), and their derivatives, prodrugs, tautomers, stereoisomers, polymorphs, solvates, hydrates, metabolites, N-oxides, pharmaceutically acceptable salts and compositions containing them.

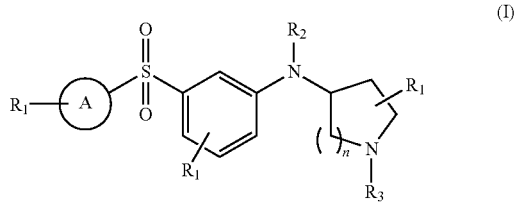

The present invention also relates to a process for the preparation of above said novel compounds, and their derivatives, prodrugs, tautomers, stereoisomers, polymorphs, solvates, hydrates, metabolites, N-oxides, pharmaceutically acceptable salts and compositions containing them.

These compounds are useful in the treatment/prevention of various disorders that are related to 5-$HT_6$ receptor functions.

BACKGROUND OF THE INVENTION

Various central nervous system disorders such as anxiety, depression, motor disorders etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity and neuroendocrine regulation among others. 5-HT receptor subtypes regulate the various effects of serotonin. Known 5-HT receptor family includes the 5-HT family (e.g. 5-$HT_{1A}$), the 5-$HT_2$ family (e.g. 5-$HT_{2A}$ & 5-$HT_{2C}$), 5-$HT_3$, 5-$HT_4$, 5-$HT_5$, 5-$HT_6$ and 5-$HT_7$ subtypes.

The 5-$HT_6$ receptor subtype was first cloned from rat tissue in 1993 (Monsma, F. J.; Shen, Y.; Ward, R. P.; Hamblin, M. W., Sibley, D. R., Molecular Pharmacology, 1993, 43, 320-327) and subsequently from human tissue (Kohen, R.; Metcalf, M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C., Biochemical Biophysical Research Communications, 1993, 193, 268-276). The receptor is found almost exclusively in the central nervous system (CNS) areas both in rats as well as in humans.

In situ hybridization studies of 5-$HT_6$ receptor in rat brain using mRNA indicate principal localization in the areas of 5-HT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-$HT_6$ receptor mRNA has been observed in the olfactory tubercle, the striatum, nucleus accumbens and dentate gyrus as well as $CA_1$, $CA_2$ and $CA_3$ regions of the hippocampus. Lower levels of 5-$HT_6$ receptor mRNA were seen in the granular layer of the cerebellum, several diencephalic nuclei, amygdala and in the cortex. Northern blots have revealed that 5-$HT_6$ receptor mRNA appears to be exclusively present in the brain, with little evidence for its presence in peripheral tissues.

Significant efforts are being made to understand the possible role of the 5-$HT_6$ receptor in psychiatry, cognitive dysfunction, motor function and control, memory, mood and the like. The compounds which demonstrate a binding affinity for the 5-$HT_6$ receptor are earnestly sought both as an aid in the study of the 5-$HT_6$ receptor and as potential therapeutic agents in the treatment of central nervous system disorders, for example see Reavill C. and Rogers D. C., Current Opinion in Investigational Drugs, 2001, 2(1): 104-109, Pharma Press Ltd.

Treatment with 5-$HT_6$ receptor antagonists increases seizure threshold in a rat maximal electroconvulsive-shock test [Stean, T. et al. (1999) Anticonvulsant properties of the selective 5-$HT_6$ receptor antagonist SB-271046 in the rat maximal electroshock seizure threshold test. Br. J. Pharmacol. 127, 131P; Routledge, C. et al. (2000) Characterization of SB-271046: a potent, selective and orally active 5-$HT_6$ receptor antagonist. Br. J. Pharmacol. 130, 1606-1612]. Although this indicates that 5-$HT_6$ receptors might regulate seizure threshold, the effect is not as pronounced as that of known anticonvulsant drugs.

Our understanding of the role of 5-$HT_6$ receptor ligands is most advanced in two therapeutic indications, learning and memory deficits and abnormal feeding behaviour, in which this receptor is likely to have a major role to play. The exact role of the 5-$HT_6$ receptor is yet to be established in other CNS indications such as anxiety; although one 5-$HT_6$ agonist has reached Phase I clinical trials recently, the exact role of the receptor is still to be established and is the focus of significant investigation. There are many potential therapeutic uses for 5-$HT_6$ receptor ligands in humans based on direct effects and on indications from available scientific studies. These studies include the localization of the receptor, the affinity of ligands with known in-vivo activity and various animal studies conducted so far. Preferably, antagonist compounds of 5-$HT_6$ receptors are sought after as therapeutic agents.

One potential therapeutic use of modulators of 5-$HT_6$ receptor functions is in the enhancement of cognition and memory in human diseases such as Alzheimer's. The high levels of receptor found in structures such as the forebrain, including the caudate/putamen, hippocampus, nucleus accumbens and cortex suggests a role for the receptor in memory and cognition since these areas are known to play a vital role in memory (Gerard, C.; Martres, M. P.; Lefevre, K.; Miquel, M. C.; Verge, D.; Lanfumey, R.; Doucet, E.; Hamon, M.; El Mestikawy, S., Brain Research, 1997, 746, 207-219). The ability of known 5-$HT_6$ receptor ligands to enhance cholinergic transmission also supports the potential cognition use (Bentley, J. C.; Boursson, A.; Boess, F. G.; Kone, F. C.; Marsden, C. A.; Petit, N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating the levels of noradrenaline, dopamine or 5-HT. This selective elevation of certain neurochemicals is noted during memory and cognition, strongly suggests a role for 5-HT$_6$ ligands in cognition (Dawson, L. A.; Nguyen, H. Q.; Li, P. British Journal of Pharmacology, 2000, 130 (1), 23-26). Animal studies of memory and learning with a known selective 5-HT$_6$ antagonist has some positive effects (Rogers, D. C.; Hatcher, P. D.; Hagan, J. J. Society of Neuroscience, Abstracts, 2000, 26, 680).

A related potential therapeutic use for 5-HT$_6$ ligands is in the treatment of attention deficit disorders (ADD, also known as Attention Deficit Hyperactivity Disorder or ADHD) in children as well as adults. As 5-HT$_6$ antagonists appear to enhance the activity of the nigrostriatal dopamine pathway and ADHD has been linked to abnormalities in the caudate (Ernst, M; Zametkin, A. J.; Matochik, J. H.; Jons, P. A.; Cohen, R. M., Journal of Neuroscience, 1998, 18(15), 5901-5907), 5-HT$_6$ antagonists may attenuate attention deficit disorders.

At present, a few fully selective agonists are available. The Wyeth agonist WAY-181187 is currently in Phase I trials to target anxiety [Cole, D. C. et al. (2005) Discovery of a potent, selective and orally active 5-HT$_6$ receptor agonist, WAY-181187. 230th ACS Natl. Meet. (August 28-September 1, Washington D.C.), Abstract MEDI 17.]

International Patent Publication WO 03/066056 A1 reports that antagonism of 5-HT$_6$ receptor could promote neuronal growth within the central nervous system of a mammal. Another International Patent Publication WO 03/065046 A2 discloses new variant of human 5-HT$_6$ receptor and proposes that 5-HT$_6$ receptor is associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A.; Blackburn, T. P., Annual Reviews in Pharmacology and Toxicology, 2000, 40, 319-334).

Further, recent in-vivo studies in rats indicate that 5-HT$_6$ modulators may be useful in the treatment of movement disorders including epilepsy (Stean, T.; Routledge, C.; Upton, N., British Journal of Pharmacology, 1999, 127 Proc. Supplement-131P; and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M.; British Journal of Pharmacology, 2000, 30 (7), 1606-1612).

Taken together, the above studies strongly suggest that compounds which are 5-HT$_6$ receptor modulators, i.e. ligands, may be useful for therapeutic indications including, the treatment of diseases associated with a deficit in memory, cognition and learning such as Alzheimer's and attention deficit disorder; the treatment of personality disorders such as schizophrenia; the treatment of behavioral disorders, e.g. anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol and other substances of abuse.

Such compounds are also expected to be of use in the treatment of certain gastrointestinal (GI) disorders such as functional bowel disorder. See for example, Roth, B. L.; et al., Journal of Pharmacology and Experimental Therapeutics, 1994, 268, pages 1403-1412; Sibley, D. R.; et al., Molecular Pharmacology, 1993, 43, 320-327.

Furthermore, the effect of 5-HT$_6$ antagonist and 5-HT$_6$ antisense oligonucleotides to reduce food intake in rats has been reported, thus potentially in the treatment of obesity. See for example, Bentley, J. C.; Boursson, A.; Boess, F. G.; Kone, F. C.; Marsden, C. A.; Petit, N.; Sleight, A. J., British Journal of Pharmacology, 1999, 126 (7), 1537-1542); Wooley et al., Neuropharmacology, 2001, 41: 210-129, British Journal of Pharmacology (2006) 1-11, Petrus Johan Pauwels et al and WO 02/098878.

A review by Holenz, Jo"rg et. al., Drug Discovery Today, 11, 7/8, April 2006, Medicinal chemistry strategies to 5-HT$_6$ receptor ligands as potential cognitive enhancers and antiobesity agents, gives elaborate discussion on evolution of 5-HT$_6$ ligands. It had summarized pharmacological tools and preclinical candidates used in evaluation of 5-HT$_6$ receptor in illnesses such as schizophrenia, other dopamine-related disorders and depression and to profile the neurochemical and electrophysiological effects of either blockade or activation of 5-HT$_6$ receptors. Furthermore, they have been used to characterize the 5-HT$_6$ receptor and to investigate its distribution.

So far several clinical candidates form the part of indole-type structures and are closely related structurally to the endogenous ligand 5-HT, for example compounds by Glennon, R. A. et. al., 2-Substituted tryptamines: agents with selectivity for 5-HT$_6$ serotonin receptors, J. Med. Chem. 43, 1011-1018, 2000; Tsai, Y. et. al., N1-(Benzenesulfonyl) tryptamines as novel 5-HT$_6$ antagonists, Bioorg. Med. Chem. Lett. 10, 2295-2299, 2000; Demchyshyn L. et al., ALX-1161: pharmacological properties of a potent and selective 5-HT$_6$ receptor antagonist, 31st Annu. Meet. Soc. Neurosci. (November 10-15), Abstract 266.6, 2001; Slassi, A. et. al., Preparation of 1-(arylsulfonyl)-3-(tetrahydropyridinyl)indoles as 5-HT$_6$ receptor inhibitors, WO 200063203, 2000; Mattsson, C. et. al., Novel, potent and selective 2-alkyl-3-(1,2,3,6-tetrahydropyridin-4-yl)-1H-indole as 5-HT$_6$ receptor agonists, XVIIth International Symposium on Medicinal Chemistry, 2002; Mattsson, C. et. al., 2-Alkyl-3-(1,2,3,6-tetrahydropyridin-4-yl)-1H-indoles as novel 5-HT$_6$ receptor agonists, Bioorg. Med. Chem. Lett. 15, 4230-4234, 2005].

Structure functionality relationships are described in the section on indole-like structures and in a receptor-modeling study in which Pullagurla et. al., claim different binding sites for agonists and antagonists [Pullagurla, M. R. et al. (2004) possible differences in modes of agonist and antagonist binding at human 5-HT$_6$ receptors. Bioorganic Medicinal Chemistry Letters, 14, 4569-4573]. Most antagonists that are reported form part of the monocyclic, bicyclic and tricyclic aryl-piperazine classes [Bromidge, S. M. et. al., (1999) 5-Chloro-N-(4-methoxy-3-piperazin-1-ylphenyl)-3-methyl-2-benzothiophenesulfonamide (SB-271046): A potent, selective and orally bioavailable 5-HT$_6$ receptor antagonist. J. Med. Chem. 42, 202-205; Characterisation of SB-399885, a potent and selective 5-HT$_6$ receptor antagonist. $33^{rd}$ Annul Meet Society Neuroscience. (November 8-12, New Orleans), Abstract 576.7; Stadler, H. et al. (1999) 5-HT$_6$ antagonists: A novel approach for the symptomatic treatment of Alzheimer's disease. $37^{th}$ IUPAC Cong. Berlin, Abstract MM-7; Bonhaus, D. W. et al. (2002) Ro-4368554, a high affinity, selective, CNS penetrating 5-HT$_6$ receptor antagonist. $32^{nd}$ Annu. Meet. Soc. Neurosci., Abstract 884.5.; Beard, C. C. et al. (2002) Preparation of new indole derivatives with 5-HT$_6$ receptor affinity. WO patent 2002098857].

Ro 63-0563: Potent and selective antagonist at human and rat 5-HT$_6$ receptors. Br. J. Pharmacol. 124, (556-562). Phase II antagonist candidate from GlaxoSmithKline, SB-742457 for the therapeutic indication of cognitive dysfunction associated with Alzheimer's disease [Ahmed, M. et al. (2003) Novel compounds. WO patent 2003080580], and the Lilly compound LY-483518 [Filla, S. A. et al. (2002) Preparation of benzenesulfonic acid indol-5-yl esters as antagonists of the 5-HT$_6$ receptor, WO 2002060871]. SB-271046, the first 5-HT$_6$ receptor antagonist to enter Phase I clinical development, has been discontinued (probably because of poor penetration of the blood-brain barrier). In addition, the selective 5-HT$_6$ receptor antagonist SB-271046 is inactive in animal tests related to either positive or negative symptoms of schizophrenia [Pouzet, B. et al. (2002) Effects of the 5-HT$_6$ receptor antagonist, SB-271046, in animal models for schizophrenia. Pharmacol. Biochem. Behav. 71, 635-643].

International Patent Publications WO 2007/046112, WO 2007/020653, WO2007/138611, WO 2005/066157, WO 2004/108671, WO 2004/048331, WO 2004/048330 and WO 2004/048328 (all assigned to Suven Life Sciences Limited) describe the related prior art. Further WO 98/27081, WO 99/02502, WO 99/37623, WO 99/42465 and WO 01/32646 (all assigned to Glaxo SmithKline Beecham PLC) disclose a series of aryl sulfonamide and sulfoxide compounds as 5-HT$_6$ receptor antagonists and are claimed to be useful in the treatment of various CNS disorders. While some 5-HT$_6$ modulators have been disclosed, there continues to be a need for compounds that are useful for modulating 5-HT$_6$. In our research in area of 5-HT$_6$ receptors, we found that sulfone compounds of formula (I) demonstrate very high 5-HT$_6$ receptor affinity. Therefore, it is an object of this invention to provide compounds, which are useful as therapeutic agents in the treatment/prevention of a variety of central nervous system disorders or disorders affected by the 5-HT$_6$ receptor.

SUMMARY OF THE INVENTION

The present invention relates to novel 5-HT$_6$ receptor ligand compounds of the formula (I), and their derivatives, prodrugs, tautomers, stereoisomers, polymorphs, solvates, hydrates, N-oxides, pharmaceutically acceptable salts and compositions containing them.

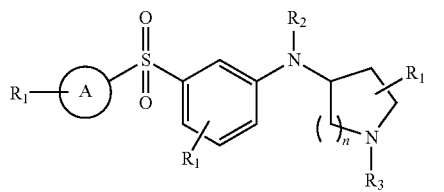

wherein ring

represents aryl or heteroaryl; with the proviso that said linkage between ring

and SO$_2$ group is not sulfonamide linkage;

$R_1$ represents hydrogen, halogen, hydroxy, oxo, thio, nitro, cyano, amide, amine, carboxylic, formyl, guanidine, alkyl, alkenyl, alkynyl, alkoxy, cycloalkyl, cycloalkylalkyl, cycloalkoxy, haloalkyl, haloalkoxy, heterocyclyl or heterocyclylalkyl;

$R_2$ represents hydrogen alkyl, cycloalkyl or cycloalkylalkyl;

$R_3$ represents hydrogen, alkyl, cycloalkyl, cycloalkylalkyl or heterocyclyl;

"n" represents 0 to 3;

The present invention relates to use of a therapeutically effective amount of compound of formula (I), to manufacture a medicament in the treatment/prevention of various disorders that are related to 5-HT$_6$ receptors.

Specifically, the compounds of this invention are useful in the treatment of various disorders such as anxiety, alzheimer's disease, depression, convulsive disorders, obsessive-compulsive disorders, cognitive memory disorders, ADHD (Attention Deficient Hyperactivity Disorder), personality disorders, psychosis, paraphrenia, psychotic depression, parkinson's disease, mania, schizophrenia, panic disorders, sleep disorders, withdrawal from drug abuse syndrome, stroke, head trauma, mild cognitive impairment, neurodegenerative disorders and obesity.

In another aspect, the invention relates to pharmaceutical compositions containing a therapeutically effective amount of at least one compound of formula (I), and their derivatives, prodrugs, tautomers, stereoisomers, polymorphs, solvates, hydrates, metabolites, N-oxides and pharmaceutically acceptable salts thereof, in admixture with at least one suitable carrier, diluents, adjuvants or excipients.

In another aspect, the invention also provides a radiolabeled compound of formula (I) for use in medical diagnosis or therapy, as well as the use of a radiolabeled compound of formula (I) to prepare a medicament useful in the treatment of various disorders that are related to 5-HT$_6$ receptors.

In another aspect, the invention relates to the use of a compound according to the present invention in combination with at least one further active ingredient for manufacture of a medicament for the treatment or prevention of diseases and conditions.

In still another aspect, the invention relates to compositions comprising and methods for using compounds of formula (I).

In yet another aspect, the invention further relates to the process for preparing compounds of formula (I) and their derivatives, prodrugs, tautomers, stereoisomers, polymorphs, solvates, hydrates, metabolites, N-oxides and pharmaceutically acceptable salts.

Representative compounds of the present invention include those specified below and their derivatives, prodrugs, tautomers, stereoisomers, polymorphs, solvates, hydrates, metabolites, N-oxides and pharmaceutically acceptable salts. The present invention should not be construed to be limited to them.

N-[2-Methyl-5-(6-chloro-1H-indole-3-yl sulfonyl)phenyl]-N-(1-methyl piperidin-4-yl)amine;

N-[2-Methyl-5-(6-chloro-1H-indole-3-yl sulfonyl)phenyl]-N-(1-methyl piperidin-4-yl)amine tartarate;

N-[5-(5-Bromo-2-methoxybenzenesulfonyl)-2-methoxyphenyl]-N-(1-methylpiperidin-4-yl)amine hydrochloride;

N-(1-Methyl piperidin-4-yl)-N-[3-(5-methoxy-1H-indole-3-yl sulfonyl)phenyl]amine;
N-(1-Methyl piperidin-4-yl)-N-[3-(6-chloro-1H-indole-3-yl sulfonyl)phenyl]amine hydrochloride;
N-(1-Methyl piperidin-4-yl)-N-[3-(5-fluoro-1H-indole-3-yl sulfonyl)phenyl]amine hydrochloride;
N-(1-Methyl piperidin-4-yl)-N-[2-methyl-5-(5-methoxy-1H-indole-3-yl sulfonyl)phenyl]amine tartrate;
N-(1-Methyl piperidin-4-yl)-N-[2-chloro-5-(6-chloro-1H-indole-3-yl sulfonyl)phenyl]amine hydrochloride;
N-(1-Methyl piperidin-4-yl)-N-[2-chloro-5-(5-methoxy-1H-indole-3-yl sulfonyl)phenyl]amine hydrochloride;
N-(1-Methyl piperidin-4-yl)-N-[3-(1H-Indole-3-yl sulfonyl)phenyl]amine;
N-(1-Methyl piperidin-4-yl)-N-[2-methoxy-5-(1H-Indole-3-yl sulfonyl)phenyl]amine;
N-(1-Methyl piperidin-4-yl)-N-[2-methyl-5-(5-methoxy-1H-Indole-3-yl sulfonyl)phenyl]amine;
N-(1-Methyl piperidin-4-yl)-N-[2-methoxy-5-(5-methoxy-1H-Indole-3-yl sulfonyl)phenyl]amine;
N-(Piperidin-4-yl)-N-[2-methoxy-5-(5-methoxy-1H-Indole-3-yl sulfonyl)phenyl]amine;
N-(1-Methyl piperidin-4-yl)-N-[2-chloro-5-(6-chloro-1H-Indole-3-yl sulfonyl)phenyl]amine;
N-(Piperidin-4-yl)-N-[2-methoxy-5-(6-chloro-1H-Indole-3-yl sulfonyl)phenyl]amine;
N-(1-Methyl piperidin-4-yl)-N-[2-methoxy-5-(6-chloro-1H-Indole-3-yl sulfonyl)phenyl]amine;
N-[5-(5-Bromo-2-methoxybenzenesulfonyl)-2-methylphenyl]-N-(3-fluoropiperidin-4-yl)amine hydrochloride;
N-[5-(3-Bromo-4-methoxybenzenesulfonyl)-2-methoxyphenyl]-N-(3-fluoropiperidin-4-yl)amine hydrochloride;
N-[5-(3-Chloro-4-methoxybenzenesulfonyl)-2-methoxyphenyl]-N-(3-fluoropiperidin-4-yl)amine hydrochloride;
N-(5-Benzenesulfonyl-2-methoxyphenyl)-N-(3-fluoropiperidin-4-yl)amine hydrochloride;
N-[5-(5-Bromo-2-methoxybenzenesulfonyl)-2-methylphenyl]-N-(piperidin-4-yl)amine hydrochloride;
N-[5-(5-Bromo-2-methoxybenzenesulfonyl)-2-methylphenyl]-N-(1-methylpiperidin-4-yl)amine hydrochloride;
N-[5-(5-Fluoro-2-methoxybenzenesulfonyl)-2-methoxyphenyl]-N-(3-fluoropiperidin-4-yl)amine hydrochloride;
N-(5-Benzenesulfonyl-2-methylphenyl)-N-(3-fluoro-1-methylpiperidin-4-yl)amine;
N-[5-(5-Bromo-2-methoxybenzenesulfonyl)-2-methoxyphenyl]-N-(3-fluoro-1-methylpiperidin-4-yl)amine;
N-(5-Benzenesulfonyl-2-methylphenyl)-N-(3-fluoropiperidin-4-yl)amine hydrochloride;
N-[5-(5-Bromo-2-methoxybenzenesulfonyl)-2-methoxyphenyl]-N-(3-fluoropiperidin-4-yl)amine hydrochloride;
N-[5-(5-Bromo-2-methoxybenzenesulfonyl)-2-methoxyphenyl]-N-(piperidin-4-yl)amine hydrochloride;
N-[5-(3-Bromo-4-methoxybenzenesulfonyl)-2-methoxyphenyl]-N-(1-methylpiperidin-4-yl)amine tartarate;
N-[5-(5-Fluoro-2-methoxybenzenesulfonyl)-2-methoxyphenyl]-N-(1-methylpiperidin-4-yl)amine tartarate;
N-[5-(4-Chlorobenzenesulfonyl)-2-methoxyphenyl]-N-(1-methylpiperidin-4-yl)amine tartarate;
N-[5-(5-Chloro-2-methoxybenzenesulfonyl)-2-methoxyphenyl]-N-(1-methylpiperidin-4-yl)amine tartarate;
N-[5-(3-Chloro-4-methoxybenzenesulfonyl)-2-methoxyphenyl]-N-(1-methylpiperidin-4-yl)amine tartarate;
N-(5-Benzenesulfonyl-2-methylphenyl)-N-(1-methylpiperidin-4-yl)amine;
N-[2-Methyl-5-(5-fluoro-1H-indole-3-yl sulfonyl)phenyl]-N-(1-methyl piperidin-4-yl)amine;
N-[2-Methyl-5-(5-fluoro-1H-indole-3-yl sulfonyl)phenyl]-N-(piperidin-4-yl)amine;
N-[2-Methoxy-5-(5-fluoro-1H-indole-3-yl sulfonyl)phenyl]-N-(1-methyl piperidin-4-yl)amine;
N-[2-Chloro-5-(5-fluoro-1H-indole-3-yl sulfonyl)phenyl]-N-(1-methyl piperidin-4-yl)amine;
N-[2-Fluoro-5-(5-fluoro-1H-indole-3-yl sulfonyl)phenyl]-N-(1-methyl piperidin-4-yl)amine;
N-[2-Methyl-5-(6-fluoro-1H-indole-3-yl sulfonyl)phenyl]-N-(1-methyl piperidin-4-yl)amine;
N-[3-(6-fluoro-1H-indole-3-yl sulfonyl)phenyl]-N-(1-methyl piperidin-4-yl)amine;
N-[2-Methoxy-5-(6-fluoro-1H-indole-3-yl sulfonyl)phenyl]-N-(1-methyl piperidin-4-yl)amine;
N-[2-Chloro-5-(6-fluoro-1H-indole-3-yl sulfonyl)phenyl]-N-(1-methyl piperidin-4-yl)amine;
N-[2-Trifluoromethyl-5-(6-fluoro-1H-indole-3-yl sulfonyl)phenyl]-N-(1-methyl piperidin-4-yl)amine;
N-[3-(5-Trifluoromethyl-1H-indole-3-yl sulfonyl)phenyl]-N-(1-methyl piperidin-4-yl)amine;
N-[2-Methyl-5-(5-Trifluoromethyl-1H-indole-3-yl sulfonyl)phenyl]-N-(1-methyl piperidin-4-yl)amine;
N-[2-Methoxy-5-(5-Trifluoromethyl-1H-indole-3-yl sulfonyl)phenyl]-N-(1-methyl piperidin-4-yl)amine;
N-[2-Chloro-5-(5-Trifluoromethyl-1H-indole-3-yl sulfonyl)phenyl]-N-(1-methyl piperidin-4-yl)amine;
N-[2-Fluoro-5-(5-Trifluoromethyl-1H-indole-3-yl sulfonyl)phenyl]-N-(1-methyl piperidin-4-yl)amine;
N-[2-Fluoro-5-(5-methoxy-1H-indole-3-yl sulfonyl)phenyl]-N-(1-methyl piperidin-4-yl)amine;
N-[2-Trifluoromethyl-5-(5-methoxy-1H-indole-3-yl sulfonyl)phenyl]-N-(1-methyl piperidin-4-yl)amine;
N-[2-Bromo-5-(5-fluoro-1H-indole-3-yl sulfonyl)phenyl]-N-(1-methyl piperidin-4-yl)amine;
N-[2-Bromo-5-(6-fluoro-1H-indole-3-yl sulfonyl)phenyl]-N-(1-methyl piperidin-4-yl)amine;
N-[2-Bromo-5-(5-trifluoromethyl-1H-indole-3-yl sulfonyl)phenyl]-N-(1-methyl piperidin-4-yl)amine;
N-[2-Bromo-5-(5-methoxy-1H-indole-3-yl sulfonyl)phenyl]-N-(1-methyl piperidin-4-yl)amine;
N-[2-Bromo-5-(6-methoxy-1H-indole-3-yl sulfonyl)phenyl]-N-(1-methyl piperidin-4-yl)amine;
N-[2-Bromo-5-(1H-indole-3-yl sulfonyl)phenyl]-N-(1-methyl piperidin-4-yl)amine;
N-[3-(5-Isopropoxy-1H-indole-3-yl sulfonyl)phenyl]-N-(1-methyl piperidin-4-yl)amine;
N-[2-Methyl-5-(5-Isopropoxy-1H-indole-3-yl sulfonyl)phenyl]-N-(1-methyl piperidin-4-yl)amine;
N-[2-Methoxy-5-(5-Isopropoxy-1H-indole-3-yl sulfonyl)phenyl]-N-(1-methyl piperidin-4-yl)amine;
N-[2-Chloro-5-(5-Isopropoxy-1H-indole-3-yl sulfonyl)phenyl]-N-(1-methyl piperidin-4-yl)amine;
N-[2-Ethoxy-5-(TH-indole-3-yl sulfonyl)phenyl]-N-(1-methyl piperidin-4-yl)amine;
N-[2-Ethoxy-5-(5-fluoro-1H-indole-3-yl sulfonyl)phenyl]-N-(1-methyl piperidin-4-yl)amine;
N-[2-Ethoxy-5-(6-methoxy-1H-indole-3-yl sulfonyl)phenyl]-N-(1-methyl piperidin-4-yl)amine;
N-[2-Ethoxy-5-(6-fluoro-1H-indole-3-yl sulfonyl)phenyl]-N-(1-methyl piperidin-4-yl)amine;
N-[2-Trifluoromethyl-3-(1H-indole-3-yl sulfonyl)phenyl]-N-(1, methyl piperidin-4-yl)amine;
N-[2-Trifluoromethyl-5-(5-chloro-1H-indole-3-yl sulfonyl)phenyl]-N-(1-methylpiperidin-4-yl)amine;
N-[2-Trifluoromethyl-5-(6-chloro-1H-indole-3-yl sulfonyl)phenyl]-N-(1-methyl piperidin-4-yl)amine;

N-[2-Trifluoromethyl-5-(6-methoxy-1H-indole-3-yl sulfonyl)phenyl]-N-(1-methyl piperidin-4-yl)amine;
N-[2-Trifluoromethoxy-3-(1H-indole-3-yl sulfonyl)phenyl]-N-(1-methyl piperidin-4-yl)amine;
N-[2-Trifluoromethoxy-5-(6-chloro-1H-indole-3-yl sulfonyl)phenyl]-N-(1-methyl piperidin-4-yl)amine;
N-[2-Trifluoromethoxy-5-(6-methoxy-1H-indole-3-yl sulfonyl)phenyl]-N-(1-methyl piperidin-4-yl)amine;
N-[2-Trifluoromethoxy-5-(5-methoxy-1H-indole-3-yl sulfonyl)phenyl]-N-(1-methyl piperidin-4-yl)amine;
N-[2-Trifluoromethoxy-5-(5-trifluoromethoxy-1H-indole-3-yl sulfonyl)phenyl]-N-(1-methyl piperidin-4-yl)amine;
N-[2-Trifluoromethoxy-5-(5-fluoro-1H-indole-3-yl sulfonyl)phenyl]-N-(1-methylpiperidin-4-yl)amine;
N-[2-Trifluoromethoxy-5-(5-chloro-1H-indole-3-yl sulfonyl)phenyl]-N-(1-methylpiperidin-4-yl)amine;
N-(1-Methyl piperidin-4-yl)-5-methyl-2-(quinoline-3-sulfonyl)-4-pyridinamine;
N-[2-Methoxy-5-(6-methoxy quinoline-3-sulfonyl)phenyl]-N-(1-methyl piperidin-4-yl)amine;
N-(3-Fluoro-1-methyl piperidin-4-yl)-[5-(7-methoxy quinoline-3-sulfonyl)-2-methyl phenyl]amine;
N-[5-(7-Methoxy isoquinoline-3-sulfonyl)-2-methyl phenyl]-N-(1-methylpyrrolidin-3-yl)amine;
N-(3-Fluoro-1-methyl piperidin-4-yl)-2-methyl-5-(6-methyl quinoline-3-sulfonyl)-3-pyridinamine;
N-[2-Methoxy-5-(6-methyl quinoline-3-sulfonyl)phenyl]-N-(1-methyl azepan-4-yl)amine;
N-[5-(7-Chloroquinoline-3-sulfonyl)-2-methyl phenyl]-N-(1-isopropyl piperidin-4-yl)amine;
N-[2-Methoxy-5-(pyridine-3-sulfonyl)phenyl]-N-(1-methyl piperidin-4-yl)amine;
N-[5-(2-Methoxy-5-methylpyridine-3-sulfonyl)-2-methyl phenyl]-N-(1-methyl piperidin-4-yl)amine;
N-(1-Methyl piperidin-4-yl)-5-Methoxy-2-(pyridine-3-sulfonyl)-4-pyridinamine;
N-(3-Fluoro-1-isopropyl piperidin-4-yl)-N-[2-methoxy-5-(pyridine-2-sulfonyl)phenyl]amine;
N-(1,3-Dimethylpiperidin-4-yl)-N-[2-fluoro-5-(6-cyanoindole-3-sulfonyl)phenyl]amine;
N-(1-Cyclopentylmethyl piperidin-4-yl)-N-[2-bromo-5-(6-cyanoindole-3-sulfonyl)phenyl]amine;
N-(1-Cyclopropyl piperidin-4-yl)-N-[3-Bromo-5-(5,6-dimethoxyindole-3-sulfonyl)-2-fluorophenyl]amine;
N-(1-Methylpiperidin-4-yl)-N-[2-ethyl-5-(6-cyanoindole-3-sulfonyl)phenyl]amine and
N-(3-Fluoro-1-methyl piperidin-4-yl)-N-[2-ethyl-5-(6-cyanoindole-3-sulfonyl)phenyl]amine;

DETAILED DESCRIPTION OF THE INVENTION

Unless otherwise stated, the following terms used in the specification and claims have the meanings given below:

The term "Halogen" means fluorine, chlorine, bromine or iodine.

The term "alkyl" means straight or branched hydrocarbon chain radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "alkenyl" means straight or branched chain aliphatic hydrocarbon group containing a carbon-carbon double bond and having 2 to 10 carbon atoms.

Exemplary "alkenyl" groups include ethenyl, 1-propenyl, 2-propenyl (allyl), iso-propenyl, 2-methyl-1-propenyl, 1-butenyl, 2-butenyl and the like.

The term "alkynyl" means straight or branched chain hydrocarbyl radical having at least one carbon-carbon triple bond and having 2 to 10 carbon atoms. Exemplary "alkynyl" groups include ethynyl, propynyl, butynyl and the like.

The term "alkoxy" means an alkyl group attached via an oxygen linkage to the rest of the molecule. Exemplary "alkoxy" groups include methoxy, ethoxy, propyloxy, iso-propyloxy and the like.

The term "Cycloalkyl" means non-aromatic mono or multi cyclic ring systems of 3 to 12 carbon atoms. Exemplary "Cycloalkyl" groups include cyclopropyl, cyclobutyl, cyclopenty and the like.

The term "Cycloalkylalkyl" means cycloalkyl group directly attached to alkyl group. Exemplary "Cycloalkylalkyl" groups include cyclopropylmethyl, cyclobutylethyl, cyclopentylethyl and the like The term "Cycloalkoxy" means non-aromatic mono or multi cyclic ring systems of 3 to 12 carbon atoms. Exemplary "Cycloalkoxy" groups include cyclopropyloxy, cyclobutyloxy, cyclopentyloxy, cyclohexyloxy and the like.

The term "Haloalkyl" means straight or branched chain alkyl radicals containing one to three carbon atoms and includes fluoromethyl, difluoromethyl, trifluoromethyl, trifluoroethyl, fluoroethyl, difluoroethyl and the like.

The term "Haloalkoxy" means straight or branched chain alkoxy radicals containing one to three carbon atoms and includes fluoromethoxy, difluoromethoxy, trifluoromethoxy, trifluoroethoxy, fluoroethoxy, difluoroethoxy and the like.

The term "Aryl" means monocyclic or bicyclic aromatic ring system, which may be substituted or unsubstituted, and optionally substituents may be selected from the group consisting of hydroxy, halogen, cyano, oxo, carboxylic, alkyl, alkoxy, haloalkyl or haloalkoxy.

The term "Heteroaryl" means organic compounds that contain a ring structure containing atoms in addition to carbon such as sulfur, oxygen or nitrogen, as part of the ring. These additional atoms may be repeated more than once in ring. These rings may be either simple aromatic rings or non-aromatic rings and includes pyridine, pyrimidine, benzothiophene, indole, benzimidazole, quinoline, tetrahydroquinoline and the like, which may be substituted or unsubstituted, and optionally substituents may be selected from the group, consisting of hydroxy, halogen, cyano, oxo, carboxylic, alkyl, alkoxy, haloalkyl or haloalkoxy.

The term "Heterocyclyl" means monocyclic or fused bicyclic compounds having 3 to 8-membered rings, whose ring structures include 1 to 3 heteroatoms, which may be substituted or unsubstituted, and optionally substituents may be selected from the group consisting of hydroxy, halogen, cyano, oxo, carboxylic, alkyl, alkoxy, haloalkyl or haloalkoxy.

The term "Heterocyclylalkyl" means heterocyclyl ring radical directly bonded to an alkyl group.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

The term "prodrug" is used to refer to a compound capable of converting, either directly or indirectly, into compounds described herein by the action of enzymes, gastric acid and the like under in vivo physiological conditions (e.g., enzymatic oxidation, reduction and/or hydrolysis).

The term "solvate" is used to describe a molecular complex between compounds of the present invention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof.

The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "tautomers" include readily interconvertible isomeric forms of a compound in equilibrium. The enol-keto tautomerism is an example.

The term "polymorphs" include crystallographically distinct forms of compounds with chemically identical structures.

The term "metabolite" refers to substance produced by metabolism.

The term "derivative" refers to a compound obtained from a compound according to formula (I), and their tautomers, stereoisomers, polymorphs, solvates, hydrates, N-oxides and pharmaceutically acceptable salts thereof, by a simple chemical process converting one or more functional groups such as by oxidation, hydrogenation, alkylation, esterification, halogenation and the like.

The term "schizophrenia" means schizophrenia, schizophreniform and schizoaffective disorder.

The term "psychotic disorder" refers to delusions, prominent hallucinations, disorganized speech or disorganized or catatonic behavior. See Diagnostic and Statistical Manual of Mental Disorder, fourth edition, American Psychiatric Association, Washington, D.C.

The terms "treating", "treat" or "treatment" embrace all the meanings such as preventative, prophylactic and palliative.

The phrase "pharmaceutically acceptable salts" indicates that the substance or composition must be compatible chemically and/or toxicologically, with the other ingredients comprising a formulation, the mammal being treated therewith.

The phrase "Therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein'.

Commercial reagents were utilized without further purification. Room temperature refers to 25-30° C. IR were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift values are expressed in parts per million ($\delta$) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The compounds of the invention can be used in combination, with each other or with other therapeutic agents or approaches used to treat or prevent the conditions listed above. Such agents or approaches include beta-secretase inhibitors; gamma-secretase inhibitors; amyloid aggregation inhibitors (e.g. Alzhemed); directly or indirectly acting neuroprotective compounds; anti-oxidants such as Vitamin E and ginkolides; anti inflammatory agents such as Cox-inhibitors or NSAID's; HMG-CoA Reductase Inhibitors (statins); acetylcholine-esterase inhibitors such as donepezil, rivastigmine, tacrine, galantamine; NMDA receptor antagonists (e.g. memantine); AMPA agonists; compounds which modulate the release or concentration of neurotransmitters (e.g. NS-2330); compounds inducing the release of growth hormones (e.g. ibutamoren mesylate and capromorelin); CBI receptor antagonists or inverse agonists; antibiotika like minocyclin or rifampicin; PDE-IV and PDE-IX inhibitors; GABAA inverse agonists; nicotinic agonists: histamin H3 antagonists, 5-HT$_4$ agonists or partial agonists; 5-HT$_6$ antagonists; $\alpha$2-adrenoreceptor antagonists; muscarinic M1 agonists; muscarinic M2 antagonists; metabotrophic glutamaic-receptor 5 positive modulators; and compounds, which modulate receptors oder enzymes in such a way, that the efficacy and/or safety of the compounds of the present invention is increased or side effects are reduced.

Preferred are such combinations comprising one or more of the compounds of the present invention and one or more additional active ingredient selected from the group consisting Alzhemed, vitamin E, ginkolide, donepezil, rivastigmine, tacrine, galantamine, memantine, NS-2330, ibutamoren mesylate, capromoreline, minocycline and rifampicine.

In the combination of the present invention, the compounds of the present invention and the above mentioned combination partners may be administered separately (e.g. kit of parts) or together in one pharmaceutical composition (e.g. capsule or tablet). In addition, the administration of one element of the combination of the present invention may be prior to, concurrent to, or subsequent to the administration of the other element of the combination. If the compounds of the present invention and the one or more additional active ingredient are present in separate formulations these separate formulations, may be administered simultaneously or sequentially.

For the treatment or prevention of the above mentioned diseases and conditions compounds of the invention can be used in combination with immunological approaches, such as, for example, immunization with A beta peptide or derivatives thereof or administration of anti-A beta peptide antibodies.

Therefore, the invention relates to the use of a compound according to the present invention in combination with at least one further active ingredient for the manufacture of a medicament for the treatment or prevention of diseases and conditions.

Numerous radioisotopes are readily available including isotopes of hydrogen, carbon, nitrogen, oxygen, phosphorus, sulfur, iodine, fluorine, bromine & chlorine. For example: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{123}$I, $^{124}$I, $^{125}$I, $^{131}$I, $^{18}$F, $^{75}$Br, $^{76}$Br, $^{77}$Br, $^{82}$Br & $^{36}$Cl.

A compound of general formula (I) can be radiolabeled by using standard techniques known in organic chemistry. Alternatively, compound of formula (I) radiolabeled with radioisotope as a substituent in one of the starting materials or in an intermediate used in the synthesis of the compound of formula (I). For example, see Arthur Murry III, D. Lloyd Williams; Organic Synthesis with Isotopes, vol. I and II, Interscience Publishers Inc., N.Y. (1958) and Melvin Calvin et al. Isotopic Carbon John Wiley and Sons Inc., N.Y. (1949).

Synthesis of radiolabeled compounds may be conveniently performed by a radioisotope supplier specializing in custom synthesis of radiolabeled probe compounds, such as Amersham Corporation, Arlington Heights, Ill.; Cambrige Isotopes Laboratories, Inc. Andover, Mass.; Wizard Laboratories, West Sacramento, Calif.; ChemSyn Laboratories, Lexena, Kans.; American Radiolabeled Chemicals, Inc.& St. Louis, Mo.;

Radioalabeled analogues of compound of formula (I) may be used in clinical studies to evaluate the role of 5-HT$_6$ receptor ligands in a variety of disease areas, where 5-HT$_6$ receptor ligands are believed to be involved.

Radiolabeled compounds of formula (I) are useful as imaging agents and biomarker for medical therapy and diagnosis. Such radiolabeled compounds are also useful as pharmacological tools for studying 5-HT$_6$ functions and activity. For example, isotopically labeled compounds are particularly useful in SPECT (single photon emission compound tomography) and in PET (positron emission tomography).

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflators. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule; it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament, along with conventional pharmaceutical auxiliaries, carriers and additives.

Such a therapy includes multiple choices: for example, administering two compatible compounds simultaneously in a single dose form or administering each compound individually in a separate dosage; or if required at same, time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Method of Preparation

The compounds of formula (I) can be prepared by Scheme-I as shown below. Wherein the key intermediate (II) is synthesized by various methods known in literature.

The process of this invention includes, reductive amination of compound of formula (II),

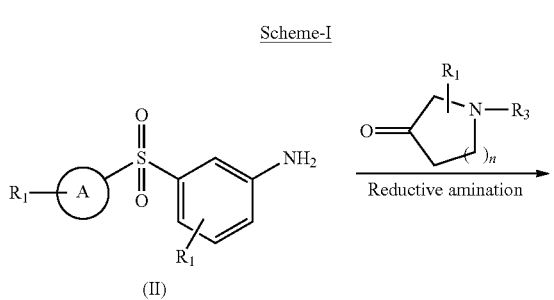

Scheme-I

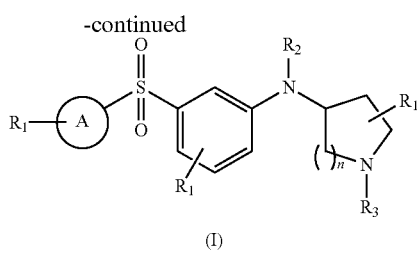

(I)

with piperidine-4-one derivatives, using a suitable reducing agent in presence of suitable solvent at suitable temperature to obtain a compound of formula (I), wherein all substitutions are described as earlier.

The above reaction is preferably carried out in a solvent such as ethanol, tetrahydrofuran, dichloromethane, dichloroethane, toluene, acetic acid, dimethylformamide, dimethyl sulfoxide and the like or a mixture thereof and preferably by using acetic acid and 1,2-dichloroethane. The reaction is carried by using reducing agents like sodium borohydride, sodium cyanoborohydride, sodium triacetoxyborohydride and the like or a mixture thereof and preferably by using sodium sulfate & sodium triacetoxyborohydride. The reaction temperature may range from 10° C. to 40° C. based on the choice of solvent and preferably at a temperature in the range from 20° C. to 30° C. The duration of the reaction may range from 2 to 6 hours, preferably from a period of 3 to 5 hours.

The key intermediate of formula (II) is synthesized as described in preparations 1 & 2. This key intermediate of formula (II) may be commercially available or they may be prepared by using known process.

Compounds obtained by the above method of preparation of the present invention can be transformed into another compound of this invention by further chemical modifications using well-known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following process can be carried out,
i) Converting a compound of the formula (I) into another compound of the formula (I)
ii) Removing any protecting groups; or
iii) Forming a pharmaceutically acceptable salt, solvate or a prodrug thereof.

Process (i) may be performed using conventional interconversion procedures such as epimerisation, oxidation, reduction, alkylation, halogenation, hydroxylation and nucleophilic or electrophilic substitution and ester hydrolysis or amide bond formation.

In process (ii) examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (eg. benzyl), which may be removed by hydrolysis (e.g. using an acid such as hydrochloric or trifluoroacetic acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl, which may be removed by base catalyzed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) pharmaceutically acceptable salts may be prepared conventionally by reaction with the appropriate acid or acid derivative as described earlier in detail.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of compound of general formula (I) containing a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid and organic acids e.g. succinic, maleic, acetic, fumaric, citric, malic, tartaric, benzoic, p-toluic, p-toluenesulfonic, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

The compounds of formula (I) may be prepared in crystalline or non-crystalline form and if crystalline, may optionally be solvated, eg. as the hydrate. This invention includes within its scope stoichiometric solvates (eg. hydrates) as well as compounds containing variable amounts of solvent (eg. water).

Various polymorphs of compound of general formula (I) forming part of this invention may be prepared by crystallization of compound of formula (I), under different conditions. For example, using different solvents commonly used or their mixtures for recrystallization; crystallizations at different temperatures; various modes of cooling ranging from very fast to very slow cooling during crystallizations. Polymorphs may also be obtained by gradual or fast cooling of compound after heating or melting. The presence of polymorphs may be determined by solid probe NMR spectroscopy, IR spectroscopy, differential scanning calorimetry, powder X-ray diffraction or such other techniques.

Pharmaceutically acceptable solvates of the compounds of formula (I) forming part of this invention may be prepared by conventional methods such as dissolving the compounds of formula (I) in solvents such as water, methanol, ethanol, mixture of solvents such as acetone-water, dioxane-water, N,N-dimethylformamide-water and the like, preferably water and recrystallizing by using different crystallization techniques.

Prodrugs of the present application may be prepared from compound of formula (I) by using known process. Conventional procedures for the selection and preparation of suitable prodrug derivatives are described, for example, in Design of prodrugs (1985); Wihnan, Biochem Soc. Trans. 1986, 14, 375-82; Stella et al., Prodrugs: A chemical approach to targeted drug delivery in directed drug delivery, 1985, 247-67, each of which is incorporated by reference herein in its entirety.

Tautomers of compounds of formula (I) can be prepared by using known process. Procedures for preparation of suitable Tautomers are described, for example in Smith M B, March J (2001). Advanced Organic Chemistry (5th ed.) New York: Wiley Interscience. pp. 1218-1223 and Katritzkv A R, Elguero J, et al. (1976). The Tautomerism of heterocycles. New York: Academic Press.

N-Oxides of compounds of formula (I) can be prepared by using known process. Procedures for preparation of suitable N-Oxides are described, March's Advanced Organic Chemistry: Reactions, Mechanisms, and Structure Michael B. Smith, Jerry March Wiley-Interscience, 5th edition, 2001.

Hydrates of compounds of formula (I) can be prepared using by known process.

In the case of the compounds of general formula (I) containing geometric isomerism the present invention relates to all of these geometric isomers.

Examples

The novel compounds of the present invention were prepared according to the following procedures, using appropriate materials and are further exemplified by the following specific examples. The most preferred compounds of the invention are any or all of those specifically set forth in these examples. These compounds are not, however, to be construed as forming the only genus that is considered as the invention and any combination of the compounds or their moieties may itself form a genus. The following examples further illustrate details for the preparation of the compounds of the present invention. Those skilled in the art will readily understand that known variations of the conditions and process of the following preparative procedures can be used to prepare these compounds.

Preparation 1: Preparation of N-[2 methyl-5-(6-chloro-1H-indole-3-yl sulfonyl)phenyl]-N-(1-methyl piperidin-4-yl)amine Step (i): Preparation of 4-methyl-3-nitro benzenesulfonyl chloride Placed chlorosulfonic acid (128 mL, 1.91 mmol) in a 500 mL four necked round bottomed flask. Then added 2-nitro toluene (65 mL, 0.547 mmol) drop wise, under stirring in 25 minutes at 25° C. The reaction mass was heated at 85° C. for 3 hours. Quenched the reaction mass into ice cold water and extracted with ethylacetate (4×250 mL), the combined organic layer was washed with brine solution (1×100 mL), dried over anhydrous sodium sulfate and solvent was removed under reduced pressure to obtain syrupy product. Yield: 109.5 grams.

IR spectra (cm$^{-1}$): 1381, 1181;

$^1$H-NMR (□ ppm): 2.76 (3H, s), 7.66-7.68 (1H, d, J=8.2 Hz), 8.14-8.17 (1H, dd, J=8.20, 2.0 Hz), 8.63 (1H, d, J=1.9 Hz).

Step (ii): Preparation of 4,4'-Dimethyl-3,3'-dinitro diphenyl disulfide

4-Methyl-3-nitro benzenesulfonyl chloride (obtained from above step) was placed in a 500 mL four necked round bottomed flask (50 grams, 0.212 mmol). Added hydroiodic acid (89 mL, 0.636 mmol), over a period of 30 minutes, through dropping funnel at 25° C. The reaction mass was heated at 110° C. for 3 hours. Then the mass was cooled to room temperature and quenched into ice cold water. Sodium bi sulfite was added in portions under efficient stirring. The solids, that separated, were filtered on buckner funnel and dissolved in dichloromethane (500 mL). The aqueous layer was removed and the organic layer was washed with brine solution (2×50 mL) and dried over anhydrous sodium sulfate. Solvent was distilled off on rotavapour under vacuum to obtain product. Yield: 22.8 grams Melting Range: 80.1-82.5° C.;

IR spectra (cm$^{-1}$): 1339, 879;

$^1$H-NMR (□ ppm): 2.57 (3H, s), 7.30-7.32 (1H, d, J=8.0 Hz), 7.59-7.61 (1H, dd, J=8.0, 1.9 Hz), 8.09 (1H, d, J=1.9 Hz).

Step (iii): Preparation of 6-chloro-3-(4-methyl-3-nitro phenyl sulfanyl)-1H-Indole Sodium hydride (950.4 mg, 19.8 mmol) was taken in a dry 100 mL three neck round bottomed flask and added dimethylformamide (3.0 mL). A solution of 6-chloro Indole (2 grams, 13 mmol) dissolved in dimethylformamide (3.0 mL) was added to the above flask in 5-10 minutes at 25° C. under nitrogen atmosphere. The reaction mass was stirred for 1 hour at 25° C., then added 4,4'-dimethyl-3,3'-dinitro diphenyl disulfide (obtained from above step) dissolved in dimethylformamide (25 mL) through dropping funnel at 5-7° C. in 30 minutes. The reaction was exothermic during addition. Then the mass was stirred over night at room temperature (25° C.). Reaction mass was quenched into ice cold water and extracted the product with ethylacetate (4×200 mL). The combined organic layer was washed with brine solution (1×100 mL), dried over anhydrous sodium sulfate and solvent was removed under reduced pressure to obtain the technical product. It was further purified by column chromatography to obtain 3.5 grams product, the eluent being 5% ethylacetate in n-hexane.

Melting Range: 151.2-153.0° C.;
IR (cm$^{-1}$): 3359, 1333;
$^1$H-NMR (☐ ppm): 2.48 (3H, s), 7.11-7.18 (3H, m), 7.43-7.46 (1H, d, J=8.5 Hz), 7.46-7.47 (1H, d, J=1.1 Hz), 7.52-7.53 (1H, d, J=2.5 Hz), 7.63 (1H, d, J=1.4 Hz), 8.51 (1H, bs);
Mass (m/z): 317.1 [M–H$^+$].

Step (iv): Preparation of 6-chloro-3-(4-methyl-3-nitro benzenesulfonyl)-1H-Indole Placed m-chloroperoxy benzoic acid (6.5 grams, 37.68 mmol) in a 100 mL three neck round bottomed flask followed by dichloromethane (15.0 mL). A solution of 6-chloro-3-(4-methyl-3-nitro phenyl sulfanyl)-1H-indole (obtained from above step) (3.0 grams, 9.4 mmol) dissolved in 30 mL of dichloromethane, was added to the flask in 20-25 minutes, through dropping funnel. The reaction mass was stirred over night at 25° C. Then the mass was diluted with 200 mL of dichloromethane and neutralized with saturated sodium bicarbonate solution under cooling (5-10° C.). The organic layer was separated. The aqueous layer was extracted with dichloromethane (3×100 mL). The combined organic layers were washed with brine solution and dried over anhydrous sodium sulfate. Solvent was removed under reduced pressure to obtain the title product.

Yield: 2.85 grams.
Melting Range: 139.6-145.0° C.;
IR (cm$^{-1}$): 3295, 1316, 1341;
$^1$H-NMR (☐ ppm): 2.62 (3H, s), 7.45 (1H, d, J=1.3 Hz), 7.58-7.60 (1H, d, J=8.0 Hz), 7.82-7.84 (1H, d, J=8.6 Hz), 7.96-7.95 (1H, d, J=2.9 Hz), 7.98-8.00 (1H, d, J=7.5 Hz), 8.11-8.14 (1H, dd, J=8.0, 1.6 Hz), 8.55-8.56 (1H, d, J=1.6 Hz), 8.95 (1H, bs);
Mass (m/z): 349.2 [M–H$^+$].

Step (v): Preparation of 5-(6-chloro-1H-indole-3-yl sulfonyl)-2-methyl phenyl amine To a 250 mL round bottomed flask, added Iron powder (1.56 grams, 27.9 mmol), 10 mL demineralized water and heated to 90-95° C. At this temperature, 4 mL of concentrated hydrochloric acid was added drop wise. The mass was further heated at 90-95° C. for 1 hour. Then cooled the mass to 60° C. and added absolute ethanol (25 mL). A solution of 6-chloro-3-(4-methyl-3-nitro benzenesulfonyl)-1H-indole (obtained from above step) (2.8 grams, 7.9 mmol) in 10 mL absolute ethanol was added lot wise over a period of 15 minutes. Then the mass was refluxed for 3 hours at 80° C. The mass was cooled to 25° C., added ethylacetate (200 mL) and stirred for 5 minutes. The reaction mass was then filtered through buckner funnel, washed with ethylacetate (3×50 mL). Aqueous layer separated from the filtrate and the organic layer was washed with brine solution (1×50 mL), dried over anhydrous sodium sulfate and solvent was concentrated to obtain oily mass. The technical product was further purified by column chromatography to obtain the title product, the eluent being 70% ethylacetate and 30% n-hexane. Yield: 1.47 grams IR (cm$^{-1}$): 3392, 3005, 1301;
$^1$H-NMR (☐ ppm): 2.01 (3H, s), 5.32 (2H, bs), 6.97-7.00 (1H, d, J=7.7, 1.7 Hz), 7.03-7.05 (1H, d, J=7.8 Hz), 7.15 (1H, d, J=1.7 Hz), 7.19-7.22 (1H, dd, J=8.5, 1.8 Hz), 7.52-7.53 (1H, d, J=1.7 Hz), 7.69-7.71 (1H, d, J=8.5 Hz), 8.08-8.09 (1H, d, J=2.9 Hz), 8.25 (1H, bs);
Mass (m/z): 319.4 [M–H$^+$].

Preparation 2: N-[5-(5-Bromo-2-methoxybenzenesulfonyl)-2-methoxyphenyl]-N-(1-methylpiperidin-4-yl)amine Step (i): Preparation of 2,2,2-Trifluoro-N-(2-methoxyphenyl)acetamide Placed o-Anisidine (37 grams, 300.8 mmol) in a 500 mL four necked round bottomed flask. Dichloromethane (200 mL) was added and contents were cooled to 0° C. Then added pyridine (26.2 mL, 330.8 mmol) drop wise, under stirring in 15 minutes at 0° C. The reaction mass was stirred for 15 minutes and trifluoroacetic anhydride (69.5 grams, 330.8 mmol) was added drop wise over a period of 15 minutes. Stirred the reaction mass for 1 hour at room temperature. Quenched the reaction mass into ice cold water and extracted with ethyl acetate (4×250 mL), the combined organic layers were washed with brine solution (1×100 mL), dried over anhydrous sodium sulfate and solvent was removed under reduced pressure to obtain the technical product. It was further purified by column chromatography to obtain the product the eluent being 5% ethyl acetate in n-hexane. Yield: 20 grams $^1$H-NMR (☐ ppm): 3.93 (3H, s), 6.93-6.95 (1H, d, J=8.14 Hz), 7.01-7.04 (1H, t, J=7.71 Hz), 7.16-7.20 (1H, t, J=8.07 Hz), 8.3-8.33 (1H, dd, J=8.06, 1.16 Hz), 8.57 (1H, bs);
Mass (m/z): 218.1 [M–H$^+$].

Step (ii): Preparation of 4-Methoxy-3-(2,2,2-trifluoroacetylamino)benzenesulfonyl chloride Placed chlorosulfonic acid (33 mL, 274 mmol) in a 500 mL four necked round bottomed flask. Then added, 2,2,2-Trifluoro-N-(2-methoxyphenyl)acetamide (20 grams, 91.3 mmol) in dichloro methane (100 mL) drop wise, under stirring in 45 minutes at 0° C. The reaction mass was allowed to reach room temperature and stirred for another 2 hours. Quenched the reaction mass into ice cold water and extracted with ethyl acetate (4×200 mL), the combined organic layer was washed with brine solution (1×50 mL), dried over anhydrous sodium sulfate and solvent was removed under reduced pressure to obtain syrupy product. Yield: 17.5 grams.

$^1$H-NMR (☐ ppm): 4.09 (3H, s), 7.10-7.13 (1H, d, J=8.83 Hz), 7.90-7.93 (1H, dd, J=8.82, 2.36 Hz), 8.60 (1H, s), 9.06-9.07 (1H, d, J=2.32 Hz).

Step (iii): Preparation of N-[5-(5-Bromo-2-methoxybenzenesulfonyl)-2-methoxyphenyl]-2,2,2-trifluoroacetamide In a 500 mL 3-neck round bottom flask equipped with reflux condenser, N$_2$ inlet, thermometer socket and magnetic bar inside was added 4-Methoxy-3-(2,2,2-trifluoroacetylamino)benzenesulfonyl chloride (17 grams, 53.5 mmol) in 1,2-dichloroethane (200 mL). To the stirred solution of above reactions mass, Aluminium chloride (7.86 grams, 58.89 mmol) and 4-bromo anisole (20 grams, 107 mmol) were added slowly. Then the reaction mass was stirred under reflux temperature for 20 hours. Reaction mass was quenched into ice cold water and acidified with 2N hydrochloric acid (50 mL) until the pH was ~4 and extracted the product with ethyl acetate (3×200 mL). The combined organic layers were washed with brine solution (1×50 mL), dried over anhydrous sodium sulfate and solvent was removed under reduced pressure to obtain the technical product. It was further purified by column chromatography to obtain the title product, the eluent being 15% ethyl acetate in n-hexane. Yield: 18.4 grams $^1$H-NMR ($\square$ ppm): 3.89 (3H, s), 4.02 (3H, s), 6.80-6.83 (1H, d, J=8.81 Hz), 7.01-7.03 (1H, d, J=8.8 Hz), 7.60-7.63 (1H, dd, J=2.46, 8.78 Hz), 7.83-7.86 (1H, dd, J=8.72, 2.2 Hz), 8.23-8.24 (1H, d, J=2.45 Hz), 8.50 (1H, bs), 9.00-9.01 (1H, d, J=2.16 Hz);

Mass (m/z): 468.0 [M+H$^+$].

Step (iv): Preparation of 5-(5-Bromo-2-methoxybenzenesulfonyl)-2-methoxyaniline

In a 500 mL 3-neck round bottom flask equipped with reflux condenser, addition funnel, thermometer socket and magnetic bar inside was added N-[5-(5-Bromo-2-methoxybenzenesulfonyl)-2-methoxyphenyl]-2,2,2-trifluoroacetamide (18.0 grams, 38.54 mmol) in methanol (200 mL). The contents of the flask were cooled to 5° C. and 6N sodium hydroxide (3.1 grams dissolved in 12.4 mL) solution (3.1 grams, 77 mmol) was added slowly over a period of 30 minutes at 5° C. The reaction mass was bought to room temperature and refluxed the reaction mass for 3 hours at 70° C. Reaction mass was cooled to room temperature and methanol was evaporated under vacuum and the obtained residue was treated with water (50 mL) and the mass was extracted with ethyl acetate (3×100 mL). The combined organic layers were washed with brine solution and dried over anhydrous sodium sulfate. Solvent was removed under reduced pressure to obtain technical product and it was further purified by recrystallisation from methanol/n-hexane to obtain the title product. Yield: 2.85 grams $^1$H-NMR ($\square$ ppm): 3.78 (3H, s), 3.90 (3H, s), 3.96 (2H, bs), 6.78-6.83 (2H, m), 7.21-7.22 (1H, d, J=2.26 Hz), 7.37-7.40 (1H, dd, J=8.44 2.2 Hz), 7.57-7.60 (1H, dd, J=8.57; 2.5 Hz), 8.21-8.22 (1H, d, J=2.46 Hz);

Mass (m/z): 371.2, 373.2 [M+H$^+$].

Step (v): Preparation of N-[5-(5-Bromo-2-methoxybenzenesulfonyl)-2-methoxyphenyl]-N-(1-methylpiperidin-4-yl)amine 5-(5-Bromo-2-methoxybenzenesulfonyl)-2-methoxyaniline (2 grams, 5.35 mmol) was added to 100 mL three necked round bottomed flask, followed by the addition of 1-methyl-4-piperidone (550 mg, 4.86 mmol), sodium sulfate (1.4 grams, 9.73 mmol) and acetic acid (40 mL) under nitrogen atmosphere. The reaction mass was stirred for 4 hours at room temperature (27° C.). Then sodium triacetoxy borohydride (3.08 grams, 14.60 mmol) was added to the reaction mass at 20-25° C. in 5 minutes. This reaction mixture was further stirred for another 2 hours at room temperature. The reaction mixture was then quenched into 100 mL water, basified to pH 9 with 50% aqueous sodium hydroxide solution under cooling (10° C.) and extracted the product with ethyl acetate (3×100 mL). The combined organic layer was washed with saturated brine solution (2×50 mL), dried over anhydrous sodium sulfate, filtered and concentrated under vacuum to obtain oily mass. The technical product was further purified by column chromatography using ethyl acetate and methanol as eluents to obtain the title product. Yield: 1.56 grams.

IR (cm$^{-1}$): 3413, 1411, 1296 and 1139;

$^1$H-NMR ($\square$ ppm): 1.47-1.53 (2H, m), 2.03-2.06 (2H, m), 2.14-2.19 (2H, m), 2.31 (3H, s), 2.80-2.82 (2H, m), 3.32-3.35 (1H, bs), 3.78 (3H, s), 3.86 (3H, s); 4.26-4.28 (1H, d, J=8.03 Hz), 6.76-6.80 (2H, m), 7.10-7.11 (1H, d, J=1.97 Hz), 7.24-7.27 (1H, m), 7.56-7.59 (1H, dd, J=8.78, 2.45 Hz), 8.21-8.22 (1H, d, 2.46 Hz);

Mass (m/z): 469.0, 471.3 [M+H$^+$].

Example 1

Preparation of N-[2-methyl-5-(6-chloro-1H-indole-3-yl sulfonyl)phenyl]-N-(1-methy piperidin-4-yl) amine 5-(6-Chloro-1H-indole-3-yl sulfonyl)-2-methyl phenyl amine [obtained from preparation 1, Step (v)](600 mg, 1.87 mmol) was added to a 100 mL three necked round bottomed flask, followed by the addition of 1-methyl-4-piperidone (423 mg, 3.74 mmol), sodium sulfate (2.6 grams, 18.7 mmol) and acetic acid (12 mL). The reaction mass was stirred for 4 hours at room temperature (30° C.). Then sodium tri acetoxy borohydride (1.18 grams, 5.61 mmol) was added to the reaction mass at 20-25° C. in 5 minutes. This reaction mixture was further stirred over night at room temperature. The reaction mixture was then quenched into 100 mL water, basified to pH 9 with 50% aqueous sodium hydroxide solution under cooling (10° C.) and extracted the product with ethylacetate (4×50 mL). The combined organic layer was washed with saturated brine solution (2×50 mL), dried over anhydrous sodium sulfate, filtered and concentrated under vacuum to obtain oily mass. The technical product was further purified by column chromatography using ethylacetate and methanol as an eluents to obtain 0.31 grams of the title product.

Melting Range: 170.3-175.0° C.;

IR (cm$^{-1}$): 3413, 1411, 1296, 1139;

$^1$H-NMR ($\square$ ppm): 1.45-1.48 (2H, m); 1.75-1.77 (2H, m); 2.02 (3H, s); 2.10-2.13 (2H, m); 2.23 (3H, s); 2.77-2.79 (2H, d); 3.26 (1H, m); 4.85-4.87 (1H, d, J=7.6 Hz); 6.95 (1H, s); 7.02-7.04 (1H, dd, J=7.7 Hz); 7.08-7.10 (1H, d, J=7.7 Hz); 7.19-7.22 (1H, dd, J=8.4, 1.6 Hz); 7.53 (1H, d, J=1.6 Hz); 7.74-7.77 (1H, d, J=8.5 Hz), 8.14 (1H, s), 12.26 (1H, bs);

Mass (m/z): 418.4 [M+H$^+$].

Example 2

Preparation of N-[2-methyl-5-(6-chloro-1H-indole-3-yl sulfonyl)phenyl]-N-(1-methyl piperidin-4-yl) amine tartarate salt N-[2-methyl-5-(6-chloro-1H-indole-3-yl sulfonyl)phenyl]-N-(1-methyl piperidin-4-yl)amine (obtained from Example 1) (360 mg, 0.86 mmol) was dissolved in methanol (10 mL), in a 50 mL round bottomed flask. L(+)-Tartaric acid (125.6 mg), dissolved in methanol (5 mL), was added drop wise at 25° C. under stirring. The reaction mass was further stirred for 1 hour at 25° C. Solvent was removed under reduced pressure to obtain 373 mg tartarate salt.

Melting Range: 155.0-159.0° C.;

IR (cm$^{-1}$): 3395, 1724, 1598, 1138, 1297;

$^1$H-NMR ($\square$ ppm): 1.40-1.45 (2H, m), 1.84-1.87 (2H, m), 2.07 (3H, s), 2.65-2.75 (2H, m), 3.08-3.11 (3H, m), 3.15 (3H, s), 4.03 (2H, s), 4.97-4.99 (1H, d, J=7.4 Hz), 7.02-7.05 (2H, m), 7.10-7.12 (1H, d, J=7.7 Hz), 7.20-7.23 (1H, dd, J=8.6, 1.6 Hz), 7.53-7.54 (1H, d, J=1.3 Hz), 7.76-7.78 (1H, d, J=8.5 Hz), 8.13 (1H, s), 12.32 (1H, bs);

Mass (m/z): 418.2 [M+H$^+$].

Example 3

Preparation of N-[5-(5-Bromo-2-methoxybenzenesulfonyl)-2-methoxyphenyl]-N-(1-methylpiperidin-4-yl)amine hydrochloride salt N-[5-(5-Bromo-2-methoxybenzenesulfonyl)-2-methoxyphenyl]-N-(1-methylpiperidin-4-yl) amine [obtained from preparation 2, Step (v)](100 mg, 0.213 mmol) was dissolved in methanol (5 mL), in a 25 mL round bottomed flask. IPA: HCl (0.1 mL, 18.23 w/w) was added drop wise at 25° C. under stirring. The reaction mass was further stirred for 1 hour at 25° C. Solvent was removed under reduced pressure and the obtained product was washed with diethyl ether (2×5 mL), decanted the ether layer and solid was dried under reduced pressure to obtain 80 mg of hydrochloride salt.

IR (cm$^{-1}$): 3395, 1724, 1598, 1297 and 1138;
$^1$H-NMR (□ ppm): 1.73-1.82 (2H, m), 2.1-2.20 (1H, m), 2.25-2.28 (2H, m), 2.89 (3H, s), 3.16-3.35 (2H, m), 3.57-3.60 (2H, m), 3.66-3.72 (1H, bs), 3.80 (3H, s), 3.94 (3H, s), 7.01-7.07 (2H, m), 7.21-7.22 (1H, d, J=1.51 Hz), 7.36-7.39 (1H, m), 7.71-7.74 (1H, dd, J=8.79, 2.40 Hz), 8.10-8.11 (1H, d, 2.26 Hz);

Mass (m/z): 469.0, 471.0 [M+H$^+$].

Examples 4-34

The compounds of Examples 4-35 were prepared by following the procedure as described in Example 1 to 3, with some non-critical variations

| | | |
|---|---|---|
| 4. | N-(1-Methyl piperidin-4-yl)-N-[3-(5-methoxy-1H-indole-3-yl sulfonyl)phenyl]amine; | IR (cm$^{-1}$): 3392, 1484, 1287, 1135;<br>$^1$H-NMR (□ ppm): 1.49-1.52 (2H, m), 1.86-1.96 (2H, m), 2.48-2.49 (3H, s), 2.87 (2H, m), 3.15 (2H, m), 3.76 (3H, s), 4.1 (1H, m), 6.20-6.22 (1H, d, J = 7.8 Hz), 6.72-6.75 (1H, dd, J = 8.1, 1.7 Hz), 6.85-6.88 (1H, dd, J = 8.8, 2.3 Hz), 7.04-7.06 (1H, d, J = 7.6 Hz), 7.15 (1H, s), 7.17-7.18 (1H, d, J = 2.3 Hz), 7.19-7.23 (1H, t, J = 7.9 Hz), 7.37-7.39 (1H, d, J = 8.8 Hz), 8.0-8.01 (1H, d, J = 2.9 Hz), 12.11 (1H, bs);<br>Mass (m/z): 400.5 [M + H$^+$]. |
| 5. | N-(1-Methyl piperidin-4-yl)-N-[3-(6-chloro-1H-indole-3-yl sulfonyl)phenyl]amine hydrochloride; | IR (cm$^{-1}$): 3434, 3293, 1298, 1132, 726;<br>$^1$H-NMR (□ ppm): 1.6 (2H, m), 1.99 (2H, m), 2.72-2.73 (3H, s), 3.2 (2H, m), 3.38-3.42 (2H, m), 3.5 (1H, m), 6.74-6.77 (1H, dd, J = 8.1, 1.8 Hz), 7.04-7.06 (1H, d, J = 7.8 Hz), 7.13 (1H, s), 7.21-7.25 (2H, m), 7.55-7.56 (1H, d, J = 1.6 Hz), 7.73-7.75 (1H, d, J = 8.5 Hz), 8.12-8.13 (1H, d, J = 2.9 Hz), 9.71 (1H, bs), 12.35 (1H, s);<br>Mass (m/z): 404.3 [M + H$^+$]. |
| 6. | N-(1-Methyl piperidin-4-yl)-N-[3-(5-fluoro-1H-indole-3-yl sulfonyl)phenyl]amine hydrochloride; | Melting Range: 229.7-233.1° C.;<br>IR (cm$^{-1}$): 3432, 3101, 2653, 1301, 1138;<br>$^1$H-NMR (□ ppm): 1.8 (2H, m), 1.99-2.02 (2H, m), 2.70-2.71 (3H, d), 3.03-3.06 (2H, m), 3.38-3.41 (2H, d), 3.7 (1H, m), 6.75-6.78 (1H, dd, J = 8.2, 2.0 Hz), 7.05-7.07 (1H, d, J = 7.4 Hz), 7.09-7.12 (1H, dd, J = 9.2, 2.6 Hz), 7.17 (1H, s), 7.21-7.25 (1H, m), 7.43-7.46 (1H, dd, J = 9.5, 2.5 Hz), 7.50-7.53 (1H, m), 8.15-8.16 (1H, d, J = 3.0 Hz), 10.34 (1H, bs), 12.41 (1H, bs);<br>Mass (m/z): 388.3 [M + H$^+$]. |
| 7. | N-(1-Methyl piperidin-4-yl)-N-[2-methyl-5-(5-methoxy-1H-indole-3-yl sulfonyl) phenyl] amine tartarate; | Melting Range: 228.6-232.2° C.;<br>IR (cm$^{-1}$): 1464, 1175, 1122;<br>$^1$H-NMR (□ ppm): 1.60-1.65 (2H, m), 1.86-1.89 (2H, m), 2.07 (3H, s), 2.52 (2H, m), 2.65 (2H, m), 3.09-3.12 (1H, m), 3.15 (3H, s), 3.76 (3H, s), 4.07 (2H, s), 4.96-4.98 (1H, d, J = 7.5 Hz), 6.85-6.88 (1H, dd, J = 8.8, 2.4 Hz), 7.04-7.06 (2H, m), 7.10-7.12 (1H, d, J = 7.60 Hz), 7.19-7.20 (1H, d, J = 2.26 Hz), 7.36-7.38 (1H, d, J = 8.88 Hz), 8.00-8.01 (1H, d, J = 2.88 Hz), 12.04 (1H, bs);<br>Mass (m/z): 414.3 [M + H$^+$]. |
| 8. | N-(1-Methyl piperidin-4-yl)-N-[2-chloro-5-(6-chloro-1H-indole-3-yl sulfonyl)phenyl]amine hydrochloride; | Melting Range: 189.7-194.2° C.;<br>IR (cm$^{-1}$): 3376, 1589, 1411, 1297;<br>$^1$H-NMR (□ ppm): 1.52-1.55 (2H, m), 1.74-1.77 (2H, m), 1.89-1.90 (2H, m), 2.28 (3H, m), 2.49-2.50 (2H, m), 3.15-3.16 (1H, m), 5.35-5.37 (1H, d, J = 7.6 Hz), 7.07-7.09 (1H, dd, J = 8.2, 2.0 Hz), 7.13-7.14 (1H, d, J = 1.78 Hz), 7.22-7.24 (1H, dd, J = 8.60, 1.80 Hz), 7.40-7.42 (1H, d, J = 8.25 Hz), 7.55-7.56 (1H, d, J = 1.72 Hz), 7.77-7.79 (1H, d, J = 8.54 Hz), 8.21 (1H, s), 12.37 (1H, bs);<br>Mass (m/z): 438.4, 440.4 [M + H$^+$]. |
| 9. | N-(1-Methyl piperidin-4-yl)-N-[2-chloro-5-(5-methoxy-1H-indole-3-yl sulfonyl)phenyl]amine hydrochloride; | Melting Range: 240.3-243.2° C.;<br>IR (cm$^{-1}$): 1589, 1293, 1138;<br>$^1$H-NMR (□ ppm): 1.54-1.57 (2H, m), 1.75-1.78 (2H, m), 2.19-2.27 (2H, m), 2.80-2.82 (2H, m), 3.15 (3H, s), 3.20 (1H, m), 3.78 (3H, s), 5.34-5.36 (1H, d, J = 7.96 Hz), 6.87-6.90 (1H, dd, J = 8.8, 2.4 Hz), 7.07-7.10 (1H, dd, J = 8.2, 2.1 Hz), 7.16-7.20 (2H, m), 7.38-7.42 (2H, m), 8.07 (1H, bs), 12.14 (1H, s);<br>Mass (m/z): 434.3, 436.3 [M + H$^+$]. |
| 10. | N-(1-Methyl piperidin-4-yl)-N-[3-(1H-Indole-3-yl sulfonyl)phenyl]amine | IR (cm$^{-1}$): 3400, 1602, 1300, 1138;<br>$^1$H-NMR (□ ppm): 1.31-1.37 (2H, m), 1.77-1.80 (2H, m), 1.98-2.01 (2H, m), 2.16 (3H, s), 2.48-2.68 (2H, s), 3.13-3.15 (1H, m), 6.02-6.04 (1H, d, J = 7.77 Hz), 6.68-6.70 (1H, dd, J = 8.24, 1.61 Hz), 7.01-7.03 (1H, d, J = 7.64 Hz), 7.09 (1H, m), 7.16-7.24 (3H, m), 7.47-7.49 (1H, d, J = 7.92 Hz), 7.74-7.76 (1H, d, 7.96 Hz), 8.09 (1H, s), 12.02 (1H, bs);<br>Mass (m/z): 370.3 [M + H$^+$]. |

| | |
|---|---|
| 11. N-(1-Methyl piperidin-4-yl)-N-[2-methoxy-5-(1H-Indole-3-yl sulfonyl)phenyl]amine | IR (cm$^{-1}$): 3378, 1598, 1308, 1129;<br>$^1$H-NMR (☐ ppm): 1.34-1.42 (2H, m), 1.72-1.75 (2H, m), 2.02-2.05 (2H, m), 2.16 (3H, s), 2.67-2.69 (2H, s), 3.42 (1H, m), 3.76 (3H, s), 4.85-4.87 (1H, d, J = 8.2 Hz), 6.86-6.88 (1H, d, J = 8.4 Hz), 6.95-6.96 (1H, bs), 7.12-7.22 (3H, m), 7.44-7.46 (1H, d, J = 7.96 Hz), 7.73-7.75 (1H, d, J = 7.79 Hz), 8.06 (1H, bs), 12.11 (1H, s);<br>Mass (m/z): 400.4 [M + H$^+$]. |
| 12. N-(1-Methyl piperidin-4-yl)-N-[2-methyl-5-(5-methoxy-1H-Indole-3-yl sulfonyl)phenyl]amine; | IR (cm$^{-1}$): 3385, 1602, 1318, 1135;<br>$^1$H-NMR (☐ ppm): 1.48 (2H, m), 1.74 (2H, m), 2.02-2.04 (2H, m), 2.05 (3H, s), 2.18 (3H, s), 2.7-2.75 (2H, m), 3.76 (3H, s), 4.82-4.85 (1H, d, J = 7.96 Hz), 6.85-6.88 (1H, dd, J = 8.92, 2.52 Hz), 6.97-6.98 (1H, bs), 7.01-7.04 (1H, dd, J = 7.64, 1.68 Hz), 7.08-7.10 (1H, d, J = 7.72 Hz), 7.19 (1H, d, J = 2.4 Hz), 7.36-7.38 (1H, d, J = 8.44 Hz), 8.00 (1H, d, J = 2.64 Hz), 12.02 (1H, s);<br>Mass (m/z): 414.3 [M + H$^+$]. |
| 13. N-(1-Methyl piperidin-4-yl)-N-[2-methoxy-5-(5-methoxy-1H-Indole-3-yl sulfonyl)phenyl]amine; | IR (cm$^{-1}$): 3405, 1589, 1291, 1134;<br>$^1$H-NMR (☐ ppm): 1.36-1.42 (2H, m), 1.72-1.75 (2H, m), 1.93-1.97 (2H, m), 2.15 (3H, s), 2.65-2.68 (2H, s), 3.77 (3H, s), 3.78 (3H, s), 4.86-4.88 (1H, d, J = 8.16 Hz), 6.84-6.87 (1H, dd, J = 8.88, 2.48 Hz), 6.88-6.90 (1H, d, J = 8.44 Hz), 6.95-6.96 (1H, d, J = 2.12 Hz), 7.13-7.16 (1H, dd, J = 8.36, 2.16 Hz), 7.19-7.20 (1H, d, J = 2.40 Hz), 7.35-7.37 (1H, d, J = 8.84 Hz), 8.00 (1H, s), 11.99 (1H, s);<br>Mass (m/z): 430.5 [M + H$^+$]. |
| 14. N-(Piperidin-4-yl)-N-[2-methoxy-5-(5-methoxy-1H-Indole-3-yl sulfonyl)phenyl]amine; | IR (cm$^{-1}$): 3374, 1596, 1294, 1136;<br>$^1$H-NMR (☐ ppm): 1.56-1.60 (2H, m), 1.90-1.93 (2H, m), 3.00-3.01 (2H, m), 3.24-3.27 (2H, s), 3.56-3.57 (1H, m), 3.76 (3H, s), 3.79 (3H, s), 5.20-5.22 (1H, d, J = 8.24 Hz), 6.85-6.87 (1H, d, J = 8.48, 2.44 Hz), 6.90-6.92 (1H, d, J = 8.48 Hz), 7.06-7.07 (1H, d, J = 2.44 Hz), 7.16-7.19 (1H, dd, J = 8.36, 2.08 Hz), 7.20-7.21 (1H, d, J = 2.44 Hz), 7.36-7.38 (1H, d, J = 8.92 Hz), 7.99 (1H, bs), 12.05 (1H, s);<br>Mass (m/z): 416.5 [M + H$^+$]. |
| 15. N-(1-Methyl piperidin-4-yl)-N-[2-chloro-5-(6-chloro-1H-Indole-3-yl sulfonyl)phenyl] amine; | Melting Range: 186.1-189.9° C.;<br>IR (cm$^{-1}$): 3377, 1589, 1297, 1146;<br>$^1$H-NMR (☐ ppm): 1.70 (2H, m), 1.88 (2H, m), 2.02 (2H, m), 2.17 (3H, s), 2.68-2.71 (2H, s), 3.25-3.26 (1H, m), 5.29-5.31 (1H, d, J = 8.04 Hz), 7.06-7.09 (1H, dd, J = 8.24, 2.12 Hz), 7.11 (1H, d, J = 1.98 Hz), 7.21-7.24 (1H, dd, J = 8.64, 1.92 Hz), 7.39-7.42 (1H, d, J = 8.08 Hz), 7.55 (1H, d, J = 1.88 Hz), 7.76-7.78 (1H, d, 8.56 Hz), 8.21 (1H, s), 12.0 (1H, bs);<br>Mass (m/z): 438.4, 440.4 [M + H$^+$]. |
| 16. N-(Piperidin-4-yl)-N-[2-methoxy-5-(6-chloro-1H-Indole-3-yl sulfonyl)phenyl] amine; | Melting Range: 208.0-208.9° C.;<br>IR (cm$^{-1}$): 3393, 1597, 1300, 1142;<br>$^1$H-NMR (☐ ppm): 1.17-1.21 (2H, m), 1.96-1.99 (2H, m), 2.58-2.59 (2H, m), 3.08-3.11 (2H, m), 3.30-3.40 (1H, m), 3.85 (3H, s), 4.32-4.34 (1H, d, J = 8.08 Hz), 6.75-6.75 (1H, d, J = 8.44 Hz), 7.07-7.08 (1H, d, J = 2.16 Hz), 7.13-7.16 (1H, dd, J = 8.52, 1.84 Hz), 7.24-7.27 (1H, dd, J = 8.36, 2.16 Hz), 7.44 (1H, d, J = 1.64 Hz), 7.78-7.81 (2H, m), 12.01 (1H, bs);<br>Mass (m/z): 420.4, 422.4 [M + H$^+$]. |
| 17. N-(1-Methyl piperidin-4-yl)-N-[2-methoxy-5-(6-chloro-1H-Indole-3-yl sulfonyl) phenyl] amine; | Melting Range: 88.6-91.6° C.;<br>IR (cm$^{-1}$): 3394, 1596, 1300, 1139;<br>$^1$H-NMR (☐ ppm): 1.6-1.7 (2H, m), 2.02-2.03 (2H, m), 2.04 (3H, m), 2.43-2.46 (2H, m), 3.0-3.02 (2H, m), 3.39-3.42 (1H, m), 3.84 (3H, s), 6.74-6.76 (1H, d, J = 8.44 Hz), 7.09-7.10 (1H, d, J = 2.20 Hz), 7.18-7.20 (1H, dd, J = 8.60, 1.80 Hz), 7.31-7.33 (1H, dd, J = 8.4, 2.20 Hz), 7.40-7.41 (1H, d, J = 1.64 Hz), 7.83-7.86 (2H, m), 9.57 (1H, bs);<br>Mass (m/z): 432.3, 434.3 [M − H$^+$]. |
| 18. N-[5-(5-Bromo-2-methoxybenzenesulfonyl)-2-methylphenyl]-N-(3-fluoropiperidin-4-yl) amine hydrochloride; | $^1$H-NMR (☐ ppm): 1.86-1.89 (1H, m), 2.01-2.04 (1H, m), 2.18 (3H, s), 3.47 (1H, s), 3.13-3.15 (1H, m), 3.27-3.30 (1H, m), 3.45-3.51 (2H, m), 3.76 (3H, s), 3.96-4.06 (1H, m), 4.97 (1H, s), 7.08-7.11 (1H, dd, J = 7.74, 1.56 Hz), 7.13-7.15 (2H, m), 7.21-7.22 (1H, d, J = 7.92 Hz), 7.82-7.84 (1H, dd, J = 6.20, 2.58 Hz), 8.01-8.02 (1H, d, J = 2.56 Hz), 8.69-8.72 (1H, d, J = 11.0 Hz), 9.46-9.49 (1H, d, J = 10.33 Hz);<br>Mass (m/z): 457.05, 459.1 [M + H$^+$]. |
| 19. N-[5-(3-Bromo-4-methoxybenzenesulfonyl)-2-methoxyphenyl]-N-(3-fluoropiperidin-4-yl)amine hydrochloride; | $^1$H-NMR (☐ ppm): 1.87-1.88 (2H, m), 3.10-3.14 (1H, m), 3.24-3.27 (1H, m), 3.34-3.47 (2H, m), 3.55-3.61 (1H, m), 3.84 (3H, s), 3.89 (3H, s), 3.90-4.07 (1H, m), 4.86-4.98 (1H, m), 6.99-7.01 (1H, d, J = 8.37 Hz), 7.20-7.26 (3H, m), 7.88-7.90 (1H, dd, J = 10.88, 2.14 Hz), 8.09-8.10 (1H, d, J = 2.22 Hz), 8.71-8.74 (1H, d, J = 10.10 Hz), 9.65-6.68 (1H, d, J = 10.1 Hz);<br>Mass (m/z): 473.05, 475.1 [M + H$^+$]. |

-continued

| | | |
|---|---|---|
| 20. | N-[5-(3-Chloro-4-methoxybenzenesulfonyl)-2-methoxyphenyl]-N-(3-fluoropiperidin-4-yl)amine hydrochloride; | $^1$H-NMR ($\square$ ppm): 1.98-2.05 (2H, m), 2.11-2.14 (1H, m), 3.24-3.27 (2H, m), 3.45-3.47 (1H, m), 3.73-3.76 (1H, m), 3.93 (3H, m), 3.95 (3H, s), 3.96-4.06 (1H, m), 5.10 (1H, s), 7.02-7.04 (1H, d, J = 8.46 Hz), 7.18-7.19 (1H, d, J = 2.00 Hz), 7.21-7.23 (1H, d, J = 8.73 Hz), 7.31-7.33 (1H, dd, J = 8.44, 2.02 Hz), 7.83-7.86 (1H, dd, J = 8.69, 2.15 Hz), 7.91-7.92 (1H, d, J = 4.27 Hz), 8.72-8.74 (1H, m), 9.62-9.65 (1H, m); Mass (m/z): 429.2, 431.4 [M + H$^+$]. |
| 21. | N-(5-Benzenesulfonyl-2-methoxyphenyl)-N-(3-fluoropiperidin-4-yl)amine hydrochloride; | $^1$H-NMR ($\square$ ppm): 1.67-1.68 (1H, m), 2.95-2.97 (1H, m), 3.11-3.20 (2H, m), 3.27-3.32 (2H, m), 3.85 (3H, s), 4.01-4.08 (1H, m), 4.55-4.67 (1H, m), 5.00 (1H, s), 7.01-7.03 (1H, d, J = 8.44 Hz), 7.17-7.18 (1H, d, J = 2.10 Hz), 7.21-7.23 (1H, dd, J = 8.36, 1.96 Hz), 7.56-7.66 (3H, m), 7.91-7.92 (1H, d, J = 7.24 Hz), 8.70-8.72 (1H, d, J = 10.18 Hz), 9.53-9.56 (1H, d, J = 9.95 Hz); Mass (m/z): 365.2 [M + H$^+$]. |
| 22. | N-[5-(5-Bromo-2-methoxybenzenesulfonyl)-2-methylphenyl]-N-(piperidin-4-yl)amine hydrochloride; | $^1$H-NMR ($\square$ ppm): 1.66-1.74 (2H, m), 1.95-1.98 (2H, m), 2.14 (3H, s), 3.01-3.10 (2H, m), 3.27-3.31 (2H, m), 3.62-3.67 (1H, m), 3.75 (3H, s), 7.01-7.04 (2H, m), 7.12-7.17 (2H, m), 7.80-7.83 (1H, dd, J = 8.84, 2.48 Hz), 7.99-8.00 (1H, d, J = 2.46 Hz), 8.81 (1H, bs), 8.93 (1H, bs); Mass (m/z): 439.2, 441.2 [M + H$^+$]. |
| 23. | N-[5-(5-Bromo-2-methoxybenzenesulfonyl)-2-methylphenyl]-N-(1-methylpiperidin-4-yl)amine hydrochloride; | $^1$H-NMR ($\square$ ppm): 1.75-1.83 (2H, m), 1.98-2.02 (3H, m), 2.12 (3H, s), 2.71-2.73 (3H, d, J = 4.34 Hz), 3.11-3.19 (4H, m), 3.75 (3H, s), 7.00-7.05 (2H, m), 7.12-7.20 (2H, m), 7.79-7.82 (1H, dd, J = 8.72, 1.88 Hz), 7.98-7.99 (1H, d, J = 2.20 Hz), 10.15 (1H, bs); Mass (m/z): 453.1, 455.0 [M + H$^+$]. |
| 24. | N-[5-(5-Fluoro-2-methoxybenzenesulfonyl)-2-methoxyphenyl]-N-(3-fluoropiperidin-4-yl)amine hydrochloride; | $^1$H-NMR ($\square$ ppm): 1.84-1.87 (2H, m), 3.11-3.14 (2H, m), 3.25-3.28 (2H, m), 3.60-3.63 (1H, m), 3.74 (3H, s), 3.86 (3H, s), 3.91-3.95 (1H, m), 4.88-5.0 (1H, m), 7.00-7.03 (1H, d, J = 8.57 Hz), 7.12-7.13 (1H, d, J = 1.92 Hz), 7.13-7.19 (2H, m), 7.52-7.54 (1H, d, J = 8.52 Hz), 7.68-7.71 (1H, dd, J = 7.96, 3.24 Hz), 8.64-8.67 (1H, bd), 9.27-9.29 (1H, bd); Mass (m/z): 413.2 [M + H$^+$]. |
| 25. | N-(5-Benzenesulfonyl-2-methylphenyl)-N-(3-fluoro-1-methylpiperidin-4-yl)amine; | $^1$H-NMR ($\square$ ppm): 1.85-1.89 (1H, m), 1.96-1.99 (1H, m), 2.17 (3H, s), 2.27-2.30 (1H, m), 2.37 (3H, s), 2.94-2.96 (1H, m), 3.22-3.28 (1H, m), 3.51-3.58 (1H, m), 3.90-4.0 (1H, m), 4.71-4.84 (1H, m), 7.15-7.16 (1H, d, J = 5.46 Hz), 7.18-7.26 (2H, m), 7.47-7.49 (2H, d, J = 5.39 Hz), 7.54-7.57 (1H, dd, J = 7.38, 2.16 Hz), 7.90-7.93 (2H, d, J = 7.25 Hz); Mass (m/z): 363.2 [M + H$^+$]. |
| 26. | N-[5-(5-Bromo-2-methoxybenzenesulfonyl)-2-methoxyphenyl]-N-(3-fluoro-1-methylpiperidin-4-yl)amine; | $^1$H-NMR ($\square$ ppm): 1.95 (2H, m), 2.27 (2H, m), 2.41 (3H, s), 2.90-3.00 (1H, m), 3.27 (1H, m), 3.47-3.56 (1H, m), 3.78 (3H, s), 3.91 (3H, s), 4.68-4.86 (2H, m), 6.79-6.82 (2H, m), 7.08-7.09 (1H, d, J = 1.12 Hz), 7.31-7.33 (1H, d, J = 8.45 Hz), 7.59-7.61 (2H, dd, J = 8.74, 2.23 Hz), 8.22-8.23 (1H, d, J = 2.16 Hz); Mass (m/z): 487.2, 489.1 [M + H$^+$]. |
| 27. | N-(5-Benzenesulfonyl-2-methylphenyl)-N-(3-fluoropiperidin-4-yl)amine hydrochloride; | $^1$H-NMR ($\square$ ppm): 1.86-1.89 (1H, m), 1.98-2.05 (1H, m), 2.14 (3H, s), 3.12-3.15 (1H, m), 3.18 (3H, m), 3.48-3.51 (1H, m), 3.58-3.61 (1H, m), 4.90-5.00 (1H, d, J = 14.82 Hz), 7.08-7.10 (1H, d, J = 7.7 Hz), 7.14 (1H, s), 7.18-7.23 (1H, d, J = 7.82 Hz), 7.57-7.60 (2H, d, J = 7.82 Hz), 7.65-7.67 (1H, d, J = 7.39 Hz), 7.89-7.93 (2H, d, J = 7.35 Hz), 8.63-8.66 (1H, d, J = 10.48 Hz), 9.27 (1H, s); Mass (m/z): 349 [M + H$^+$]. |
| 28. | N-[5-(5-Bromo-2-methoxybenzenesulfonyl)-2-methoxyphenyl]-N-(3-fluoropiperidin-4-yl)amine hydrochloride; | $^1$H-NMR ($\square$ ppm): 1.58-1.66 (1H, m), 1.78-1.87 (1H, m), 1.95-1.98 (1H, m), 3.04-3.01 (2H, m), 3.57-3.63 (2H, m), 3.76 (3H, s), 3.84-3.86 (3H, d), 3.94-3.96 (1H, m), 4.88-4.99 (1H, m), 6.95-7.02 (2H, m), 7.12-7.23 (2H, m), 7.79-7.81 (1H, d, J = 8.76 Hz), 7.90-8.00 (1H, d, J = 2.54 Hz), 8.60-9.2 (2H, m); Mass (m/z): 473, 475.1 [M + H$^+$]. |
| 29. | N-[5-(5-Bromo-2-methoxybenzenesulfonyl)-2-methoxyphenyl]-N-(piperidin-4-yl)amine hydrochloride; | $^1$H-NMR ($\square$ ppm): 1.81-1.71 (2H, m), 2.20-2.24 (2H, m), 3.13-3.25 (2H, m), 3.35-3.36 (1H, m), 3.47-3.49 (2H, m), 3.72-3.75 (1H, m), 3.80 (3H, s), 3.95 (3H, s), 7.02-7.07 (2H, m), 7.25-7.26 (1H, d, J = 1.87 Hz), 7.39-7.42 (1H, dd, J = 8.46, 1.94 Hz), 7.71-7.74 (1H, dd, J = 8.83, 2.52 Hz), 8.10-8.11 (1H, d, J = 2.45 Hz); Mass (m/z): 455.06, 457.1 [M + H$^+$]. |
| 30. | N-[5-(3-Bromo-4-methoxybenzenesulfonyl)-2-methoxyphenyl]-N-(1-methylpiperidin-4-yl)amine tartarate; | IR (cm$^{-1}$): 3394, 1596, 1300 and 1139; $^1$H-NMR ($\square$ ppm): 1.80-1.82 (2H, m), 2.16-2.19 (2H, m), 2.85 (3H, s), 3.12-3.19 (2H, m), 3.33 (1H, s), 3.47-3.50 (2H, m), 3.66-3.69 (1H, m), 3.89 (3H, s), 3.92 (3H, s), 4.41 (3H, s), 6.94-6.96 (1H, d, J = 8.49 Hz), 7.05-7.06 (1H, d, J = 2.13 Hz), 7.14-7.16 (1H, d, J = 4.60 Hz), 7.22-7.24 (1H, dd, J = 8.40, 2.17 Hz), 7.84-7.89 (1H, dd, J = 8.70, 2.34 Hz), 8.02-8.03 (1H, d, J = 2.24 Hz); Mass (m/z): 469.3, 471.2 [M + H$^+$]. |

-continued

| | | |
|---|---|---|
| 31. N-[5-(5-Fluoro-2-methoxybenzenesulfonyl)-2-methoxyphenyl]-N-(1-methylpiperidin-4-yl)amine tartarate; | IR (cm$^{-1}$): 3394, 1596, 1300 and 1139; $^1$H-NMR (☐ ppm): 1.84-1.86 (2H, m), 2.17-2.20 (2H, m), 2.85 (3H, s), 3.13-3.18 (2H, m), 3.62-3.67 (2H, m), 3.74-3.75 (2H, m), 3.76 (3H, s), 3.90 (3H, s), 4.42 (2H, s), 6.94-6.96 (1H, d, J = 8.47 Hz), 7.08-7.12 (2H, m), 7.24-7.26 (1H, dd, J = 8.44, 2.06 Hz), 7.35-7.37 (1H, d, J = 8.21 Hz), 7.73-7.76 (1H, dd, J = 8.00, 3.24 Hz); Mass (m/z): 409.1 [M + H$^+$]. | |
| 32. N-[5-(4-Chlorobenzenesulfonyl)-2-methoxyphenyl]-N-(1-methylpiperidin-4-yl)amine tartarate; | IR (cm$^{-1}$): 3394, 1596, 1300, 1139; $^1$H-NMR (☐ ppm): 1.82-1.84 (2H, m), 2.15-2.18 (2H, m), 2.85 (3H, s), 3.12-3.29 (2H, m), 3.33 (1H, m), 3.45-3.50 (2H, m), 3.65-3.70 (1H, m), 3.89 (3H, s), 4.41 (2H, s), 6.95-6.97 (1H, d, J = 8.49 Hz), 7.05-7.06 (1H, d, J = 2.13 Hz), 7.24-7.26 (1H, dd, J = 8.40, 2.10 Hz), 7.53-7.56 (2H, m), 7.86-7.89 (2H, m); Mass (m/z): 395.2, 397.2 [M + H$^+$]. | |
| 33. N-[5-(5-Chloro-2-methoxybenzenesulfonyl)-2-methoxyphenyl]-N-(1-methylpiperidin-4-yl)amine tartarate; | IR (cm$^{-1}$): 3394, 1596, 1300 and 1139; $^1$H-NMR (☐ ppm): 1.84-1.86 (2H, m), 2.16-2.19 (2H, m), 2.85 (3H, s), 3.13-3.18 (2H, m), 3.48-3.51 (2H, m), 3.63-3.72 (1H, m), 3.78 (3H, s), 3.90 (3H, s), 4.42 (2H, s), 6.94-6.96 (1H, d, J = 8.53 Hz), 7.08-7.09 (1H, d, J = 1.80 Hz), 7.09-7.10 (1H, d, J = 4.81 Hz), 7.24-7.26 (1H, dd, J = 8.41, 2.01 Hz), 7.55-7.58 (1H, dd, J = 8.87, 2.70 Hz), 7.97-7.98 (1H, d, J = 2.60 Hz) Mass (m/z): 425.2, 427.2 [M + H$^+$]. | |
| 34. N-[5-(3-Chloro-4-methoxybenzenesulfonyl)-2-methoxyphenyl]-N-(1-methylpiperidin-4-yl)amine tartarate; | IR (cm$^{-1}$): 3394, 1596, 1300, 1139; $^1$H-NMR (☐ ppm): 1.83-1.85 (2H, m), 2.14-2.17 (2H, m), 2.85 (3H, s), 3.12-3.17 (2H, m), 3.48-3.50 (2H, m), 3.66-3.71 (1H, m), 3.88 (3H, s), 3.92 (3H, s), 4.42 (2H, s), 6.93-6.95 (1H, d, J = 8.44 Hz), 7.07-7.08 (1H, d, J = 1.87 Hz), 7.17-7.19 (1H, d, J = 8.75 Hz), 7.22-7.24 (1H, dd, J = 8.44, 2.06 Hz), 7.80-7.83 (1H, dd, J = 8.73, 2.25 Hz), 7.88-7.89 (1H, d, J = 2.25 Hz); Mass (m/z): 425.2 [M + H$^+$] | |
| 35. N-(5-Benzenesulfonyl-2-methylphenyl)-N-(1-methylpiperidin-4-yl)amine; | IR (cm$^{-1}$): 3398, 2937, 1587, 1303, 1149; $^1$H-NMR (☐ ppm): 1.48-1.57 (2H, m), 2.01-2.07 (2H, m), 2.11 (3H, m), 2.17-2.22 (2H, m), 2.32 (3H, m), 2.80-2.83 (2H, m), 3.57 (1H, bs), 3.59 (1H, bs), 7.10-7.13 (3H, m), 7.45-7.53 (3H, m), 7.91-7.93 (2H, m); Mass (m/z): 345.1 [M + H$^+$]. | |

Examples 36-93

The person skilled in the art can prepare the compounds of Examples 36-93 by following the procedures described above.

36. N-[2-Methyl-5-(5-fluoro-1H-indole-3-yl sulfonyl)phenyl]-N-(1-methyl piperidin-4-yl)amine;
37. N-[2-Methyl-5-(5-fluoro-1H-indole-3-yl sulfonyl)phenyl]-N-(piperidin-4-yl)amine;
38. N-[2-Methoxy-5-(5-fluoro-1H-indole-3-yl sulfonyl)phenyl]-N-(1-methyl piperidin-4-yl)amine;
39. N-[2-Chloro-5-(5-fluoro-1H-indole-3-yl sulfonyl)phenyl]-N-(1-methyl piperidin-4-yl)amine;
40. N-[2-Fluoro-5-(5-fluoro-1H-indole-3-yl sulfonyl)phenyl]-N-(1-methyl piperidin-4-yl)amine;
41. N-[2-Methyl-5-(6-fluoro-1H-indole-3-yl sulfonyl)phenyl]-N-(1-methyl piperidin-4-yl)amine;
42. N-[3-(6-fluoro-1H-indole-3-yl sulfonyl)phenyl]-N-(1-methyl piperidin-4-yl)amine;
43. N-[2-Methoxy-5-(6-fluoro-1H-indole-3-yl sulfonyl)phenyl]-N-(1-methyl piperidin-4-yl)amine;
44. N-[2-Chloro-5-(6-fluoro-1H-indole-3-yl sulfonyl)phenyl]-N-(1-methyl piperidin-4-yl)amine;
45. N-[2-Trifluoromethyl-5-(6-fluoro-1H-indole-3-yl sulfonyl)phenyl]-N-(1-methyl piperidin-4-yl)amine;
46. N-[3-(5-Trifluoromethyl-1H-indole-3-yl sulfonyl)phenyl]-N-(1-methyl piperidin-4-yl)amine;
47. N-[2-Methyl-5-(5-Trifluoromethyl-1H-indole-3-yl sulfonyl)phenyl]-N-(1-methyl piperidin-4-yl)amine;
48. N-[2-Methoxy-5-(5-Trifluoromethyl-1H-indole-3-yl sulfonyl)phenyl]-N-(1-methyl piperidin-4-yl)amine;
49. N-[2-Chloro-5-(5-Trifluoromethyl-1H-indole-3-yl sulfonyl)phenyl]-N-(1-methyl piperidin-4-yl)amine;
50. N-[2-Fluoro-5-(5-Trifluoromethyl-1H-indole-3-yl sulfonyl)phenyl]-N-(1-methyl piperidin-4-yl)amine;
51. N-[2-Fluoro-5-(5-methoxy-1H-indole-3-yl sulfonyl)phenyl]-N-(1-methyl piperidin-4-yl)amine;
52. N-[2-Trifluoromethyl-5-(5-methoxy-1H-indole-3-yl sulfonyl)phenyl]-N-(1-methyl piperidin-4-yl)amine;
53. N-[2-Bromo-5-(5-fluoro-1H-indole-3-yl sulfonyl)phenyl]-N-(1-methyl piperidin-4-yl)amine;
54. N-[2-Bromo-5-(6-fluoro-1H-indole-3-yl sulfonyl)phenyl]-N-(1-methyl piperidin-4-yl)amine;
55. N-[2-Bromo-5-(5-trifluoromethyl-1H-indole-3-yl sulfonyl)phenyl]-N-(1-methyl piperidin-4-yl)amine;
56. N-[2-Bromo-5-(5-methoxy-1H-indole-3-yl sulfonyl)phenyl]-N-(1-methyl piperidin-4-yl)amine;
57. N-[2-Bromo-5-(6-methoxy-1H-indole-3-yl sulfonyl)phenyl]-N-(1-methyl piperidin-4-yl)amine;
58. N-[2-Bromo-5-(1H-indole-3-yl sulfonyl)phenyl]-N-(1-methyl piperidin-4-yl)amine;
59. N-[3-(5-Isopropoxy-1H-indole-3-yl sulfonyl)phenyl]-N-(1-methyl piperidin-4-yl)amine;
60. N-[2-Methyl-5-(5-Isopropoxy-1H-indole-3-yl sulfonyl)phenyl]-N-(1-methyl piperidin-4-yl)amine;

-continued

61. N-[2-Methoxy-5-(5-Isopropoxy-1H-indole-3-yl sulfonyl)phenyl]-N-(1-methyl piperidin-4-yl)amine;
62. N-[2-Chloro-5-(5-Isopropoxy-1H-indole-3-yl sulfonyl)phenyl]-N-(1-methyl piperidin-4-yl)amine;
63. N-[2-Ethoxy-5-(1H-indole-3-yl sulfonyl)phenyl]-N-(1-methyl piperidin-4-yl)amine;
64. N-[2-Ethoxy-5-(5-fluoro-1H-indole-3-yl sulfonyl)phenyl]-N-(1-methyl piperidin-4-yl)amine;
65. N-[2-Ethoxy-5-(6-methoxy-1H-indole-3-yl sulfonyl)phenyl]-N-(1-methyl piperidin-4-yl)amine;
66. N-[2-Ethoxy-5-(6-fluoro-1H-indole-3-yl sulfonyl)phenyl]-N-(1-methyl piperidin-4-yl)amine;
67. N-[2-Trifluoromethyl-3-(1H-indole-3-yl sulfonyl)phenyl]-N-(1-methyl piperidin-4-yl)amine;
68. N-[2-Trifluoromethyl-5-(5-chloro-1H-indole-3-yl sulfonyl)phenyl]-N-(1-methylpiperidin-4-yl)amine;
69. N-[2-Trifluoromethyl-5-(6-chloro-1H-indole-3-yl sulfonyl)phenyl]-N-(1-methyl piperidin-4-yl)amine;
70. N-[2-Trifluoromethyl-5-(6-methoxy-1H-indole-3-yl sulfonyl)phenyl]-N-(1-methyl piperidin-4-yl)amine;
71. N-[2-Trifluoromethoxy-3-(1H-indole-3-yl sulfonyl) phenyl]-N-(1-methyl piperidin-4-yl)amine;
72. N-[2-Trifluoromethoxy-5-(6-chloro-1H-indole-3-yl sulfonyl)phenyl]-N-(1-methyl piperidin-4-yl)amine;
73. N-[2-Trifluoromethoxy-5-(6-methoxy-1H-indole-3-yl sulfonyl)phenyl]-N-(1-methy lpiperidin-4-yl)amine;
74. N-[2-Trifluoromethoxy-5-(5-methoxy-1H-indole-3-yl sulfonyl)phenyl]-N-(1-methyl piperidin-4-yl)amine;
75. N-[2-Trifluoromethoxy-5-(5-trifluoromethoxy-1H-indole-3-yl sulfonyl) phenyl]-N-(1-methyl piperidin-4-yl)amine;
76. N-[2-Trifluoromethoxy-5-(5-fluoro-1H-indole-3-yl sulfonyl) phenyl]-N-(1-methylpiperidin-4-yl)amine;
77. N-[2-Trifluoromethoxy-5-(5-chloro-1H-indole-3-yl sulfonyl) phenyl]-N-(1-methylpiperidin-4-yl)amine;
78. N-(1-Methyl piperidin-4-yl)-5-methyl-2-(quinoline-3-sulfonyl)-4-pyridinamine;
79. N-[2-Methoxy-5-(6-methoxy quinoline-3-sulfonyl)phenyl]-N-(1-methyl piperidin-4-yl)amine;
80. N-(3-Fluoro-1-methyl piperidin-4-yl)-[5-(7-methoxy quinoline-3-sulfonyl)-2-methyl phenyl]amine;
81. N-[5-(7-Methoxy isoquinoline-3-sulfonyl)-2-methyl phenyl]-N-(1-methyl pyrrolidin-3-yl)amine;
82. N-(3-Fluoro-1-methyl piperidin-4-yl)-2-methyl-5-(6-methyl quinoline-3-sulfonyl)-3-pyridinamine;
83. N-[2-Methoxy-5-(6-methyl quinoline-3-sulfonyl) phenyl]-N-(1-methyl azepan-4-yl)amine;
84. N-[5-(7-Chloroquinoline-3-sulfonyl)-2-methyl phenyl]-N-(1-isopropyl piperidin-4-yl)amine;
85. N-[2-Methoxy-5-(pyridine-3-sulfonyl)phenyl]-N-(1-methyl piperidin-4-yl)amine;
86. N-[5-(2-Methoxy-5-methyl pyridine-3-sulfonyl)-2-methyl phenyl]-N-(1-methyl piperidin-4-yl)amine;
87. N-(1-Methyl piperidin-4-yl)-5-Methoxy-2-(pyridine-3-sulfonyl)-4-pyridinamine;
88. N-(3-Fluoro-1-isopropyl piperidin-4-yl)-N-[2-methoxy-5-(pyridine-2-sulfonyl)phenyl]amine;
89. N-(1,3-Dimethylpiperidin-4-yl)-N-[2-fluoro-5-(6-cyanoindole-3-sulfonyl)phenyl]amine;
90. N-(1-Cyclopentylmethyl piperidin-4-yl)-N-[2-bromo-5-(6-cyanoindole-3-sulfonyl)phenyl]amine;
91. N-(1-Cyclopropyl piperidin-4-yl)-N-[3-Bromo-5-(5,6-dimethoxyindole-3-sulfonyl)-2-fluorophenyl]amine;
92. N-(1-Methylpiperidin-4-yl)-N-[2-ethyl-5-(6-cyanoindole-3-sulfonyl)phenyl]amine;
93. N-(3-Fluoro-1-methyl piperidin-4-yl)-N-[2-ethyl-5-(6-cyanoindole-3-sulfonyl)phenyl]amine;

Biological Assays

Example 94

Determination of $K_b$ Values for 5-HT$_6$ Receptor

A stable CHO cell line expressing recombinant human 5-HT$_6$ receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds and/or agonist, cells were serum starved overnight. Increasing concentrations of test compounds were added along with 10 uM serotonin in Hams F12 medium containing 1% dialyzed FBS to the cells. The incubation was continued at 37° C. in CO$_2$ incubator for 4 hours. Medium was removed and cells were washed with phosphate buffered saline. The cells were lysed and luciferase activity was measured in a Luminometer. Luminescence units were plotted against the compound concentrations using Graphpad software. EC$_{50}$ values of the compounds were defined as the concentration required reducing the luciferase activity by 50%. The $K_b$ values were calculated by feeding the concentration of the agonist used in the assay and its EC$_{50}$ value in the same software.

| Example Number | $K_b$ (nM) |
|---|---|
| 1. | 1.55 |
| 3. | 0.01 |
| 5. | 3.38 |
| 6. | 3.59 |
| 8. | 5.70 |
| 11. | 0.05 |
| 13. | 0.11 |
| 14. | 0.16 |
| 16. | 0.22 |
| 17. | 0.82 |
| 18. | 6.1 |
| 22. | 1.1 |
| 23. | 2.1 |
| 28. | 0.1 |
| 29. | 0.1 |

-continued

| Example Number | $K_b$ (nM) |
|---|---|
| 30. | 0.01 |
| 31. | 0.05 |
| 32. | 0.06 |
| 34. | 0.1 |

Literature References: Ruth, K., Lucy, A. F., Doris, E. A. H., Chris R. G., Mark W. H. (2001). Cloning of the mouse 5-HT$_6$ serotonin receptor and mutagenesis studies of the third cytoplasmic loop. Mol. Brain. Res., 90, 110-117.
Gonzalo, R., Elisabeth, S., Marta, P., Pilar, P., Xavier. C., Jorg, H., Helmut, B., Petrus, J. P. (2006). Efficacy of selective 5-HT$_6$ receptor ligands determined by monitoring 5-HT$_6$ receptor-mediated cAMP signaling pathways. Br. J. Pharmacol., 148, 1133-1143.

Example 95

Binding Assay for Human 5-HT$_6$ Receptor

Compounds can be tested according to the following the procedures.
Materials and Methods:
Receptor source: Human recombinant expressed in HEK293 cells
Radioligand: [$^3$H]LSD (60-80 Ci/mmol)
Final ligand concentration—[1.5 nM]
Non-specific determinant: Methiothepin mesylate—[0.1 M]
Reference compound: Methiothepin mesylate
Positive control: Methiothepin mesylate
Incubation conditions: Reactions were carried out in 50 μM TRIS-HCl (pH 7.4) containing 10 μM MgCl$_2$, 0.5 mM EDTA for 60 minutes at 37° C. The reaction was terminated by rapid vacuum filtration onto the glass fiber filters. Radioactivity trapped onto the filters was determined and compared to the control values in order to ascertain any interactions of the test compound(s) with the cloned serotonin 5-HT$_6$ binding site.
Literature Reference: Monsma F. J. Jr., et al., Molecular Cloning and Expression of Novel Serotonin Receptor with High Affinity for Tricyclic Psychotropic Drugs. Mol. Pharmacol. (43): 320-327 (1993).

Example 96

5-HT$_6$ Functional Assay Cyclic AMP

The antagonist property of the compounds at the human 5-HT$_6$ receptors was determined by testing their effect on cAMP accumulation in stably transfected HEK293 cells. Binding of an agonist to the human 5-HT$_6$ receptor will lead to an increase in adenyl cyclase activity. A compound, which is an agonist will show an increase in cAMP production and a compound that is an antagonist will block the agonist effect.
Human 5-HT$_6$ receptors were cloned and stably expressed in HEK293 cells. These cells were plated in 6 well plates in DMEM/F12 media with 10% fetal calf serum (FCS) and 500 μg/mL G418 and incubated at 37° C. in a CO$_2$ incubator. The cells were allowed to grow to about 70% confluence before initiation of the experiment. On the day of the experiment, the culture media was removed and the cells were washed once with serum free medium (SFM). Two mL of SFM+IBMX media was added and incubated at 37° C. for 10 minutes. The media were removed and fresh SFM+IBMX media containing various compounds and 1 μM serotonin (as antagonist) were added to the appropriate wells and incubated for 30 minutes. Following incubation, the media were removed and the cells were washed once with 1 mL of PBS (phosphate buffered saline). Each well was treated with 1 mL cold 95% ethanol and 5 μM EDTA (2:1) at 4° C. for 1 hour. The cells were then scraped and transferred into Eppendorf tubes. The tubes were centrifuged for 5 minutes at 4° C. and the supernatants were stored at 4° C. until assayed.
cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 L, peroxidase-labeled cAMP to the sample (100 μL) pre-incubated with the antiserum (100 mL) for 2 hours at 4° C. Following 1 hour incubation at 4° C., the unbound ligand is separated by a simple washing procedure. Then an enzyme substrate, trimethylbenzidine (1), is added and incubated at room temperature for 60 minutes. The reaction is stopped by the addition of 100 mL 1.0 M sulphuric acid and the resultant color read by a microtitre plate spectrophotometer at 450 nm within 30 minutes.
In the functional adenylyl cyclase assay, some of the compound of this invention was found to be a competitive antagonist with good selectivity over a number of other receptors including other serotonin receptors such as 5-HT$_{1A}$ and 5-HT$_7$.

Example 97

Rodent Pharmacokinetic Study

Male wistar rats (230-280 grams) obtained from NIN (National Institute of Nutrition, Hyderabad, India) were used as an experimental animal. Three to five animals were housed in each cage. Animals were kept fasted over night and maintained on a 12 hours light/dark cycle. Three rats were dosed NCE (10 mg/Kg) orally and intravenously on day 0 and day 2.
At each time point blood was collected by jugular vein. Plasma was stored frozen at −20° C. until analysis. The concentrations of the NCE compound in plasma were determined using LC-MS/MS method. Schedule time points: Pre dose 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 2-2000 ng/mL in plasma. Study samples were analyzed using calibration samples in the batch and quality control samples spread across the batch.
Pharmacokinetic parameters $C_{max}$, $T_{max}$, $AUC_t$, $T_{1/2}$ and Bioavailability were calculated by non-compartmental model using software WinNonlin version 5.1.

| Ex. No. | Strain/Sex | Dose (mg/kg) | Vehicle | Route of administration | $C_{max}$ (ng/mL) | $T_{max}$ (h) | $AUC_t$ (ng · hr/mL) | $T_{1/2}$ (h) | Bioavailability (%) |
|---|---|---|---|---|---|---|---|---|---|
| 1. | Wistar/Male | 10 | Water | Oral | 128 ± 13 | 3.42 ± 2.74 | 750 ± 363 | 6.38 ± 1.38 | 31 ± 12 |
|  | Wistar/Male | 10 | Water | Intravenous | 1644 ± 582 | 0.14 ± 0.10 | 2484 ± 853 | 5.23 ± 2.08 |  |
| 3. | Wistar/Male | 10 | Water | Oral | 341 ± 60 | 0.56 ± 0.31 | 931 ± 186 | 1.35 ± 0.27 | 38 ± 1 |
|  | Wistar/Male | 10 | Water | Intravenous | 1084 ± 569 | 0.12 ± 0.09 | 1611 ± 544 | 1.57 ± 0.21 |  |
| 8. | Wistar/Male | 10 | 50% PEG 400 | Oral | 327 ± 99 | 3.00 ± 0.00 | 3806 ± 1340 | 9.06 ± 2.13 | 58 ± 12 |
|  | Wistar/Male | 10 | 50% PEG 400 | Intravenous | 1337 ± 426 | 0.08 ± 0.00 | 6953 ± 3450 | 5.64 ± 0.95 |  |
| 17. | Wistar/Male | 10 | Water | Oral | 379 ± 160 | 3.00 ± 0.00 | 1429 ± 734 | 1.86 ± 0.09 | 24 ± 2 |
|  | Wistar/Male | 10 | Water | Intravenous | 4222 ± 2252 | 0.08 ± 0.00 | 5731 ± 2622 | 3.86 ± 0.09 |  |
| 28. | Wistar/Male | 10 | Water | Oral | 429 ± 181 | 0.83 ± 0.29 | 1525 ± 630 | 1.36 ± 0.07 | 44 ± 18 |
|  | Wistar/Male | 10 | Water | Intravenous | 1923 ± 29 | 0.08 ± 0.00 | 3474 ± 161 | 1.46 ± 0.13 |  |

Example 98

Rodent Brain Penetration Study

Male Wister rats (230-280 grams) obtained from NIN (National Institute of Nutrition, Hyderabad, India) was used as an experimental animal. Three animals were housed in each cage. Animals were given water and food ad libitum throughout the experiment, and maintained on a 12 hours light/dark cycle.

Brain penetration was determined at steady state in rat. One day prior to dosing day, male wistar rats (225-250 grams) were anesthetized with halothane for surgical placement of jugular and femoral vein catheters. After surgery, the rats were housed in individual rat infusion cage connected with infusion components (Instech Solomon; Plymouth Meeting, Pa. USA) and allowed free access to food and water NCE compound was dissolved in water and administered at a constant infusion rate (5 mL/kg/hr) over 6-10 hours at a target dose rate of 1.0 mg free base/kg/h. Blood samples were removed during the latter part of the infusion to confirm steady-state blood concentrations, brain and blood was collected and estimated. Animals will be sacrificed to collect the plasma and brain tissue and was homogenized. Plasma and Brain was stored frozen at −20° C. until analysis. The concentrations of the NCE compound in plasma and Brain were determined using LC-MS/MS method.

The NCE compounds were quantified in plasma and brain homogenate by validated LC-MS/MS method using solid phase extraction technique. NCE compounds were quantified in the calibration range of 1-500 ng/mL in plasma and brain homogenate. Study samples were analyzed using calibration samples in the batch and quality control samples spread across the batch. Extents of brain-blood ratio were calculated ($C_b/C_p$).

Example 99

Rodent Brain Micro Dialysis Study for Possible Modulation of Neurotransmitters

Male Wister rats (230-280 grams) obtained from N.I.N. (National Institute of Nutrition, Hyderabad, India) was used as experimental animals.

Group allocation Group 1: Vehicle (Water; 5 mL/kg; p.o.), Group 2: NCE (3 mg/kg; p.o.), Group 3: NCE (10 mg/kg; p.o.)

Surgical Procedure: Rats were anesthetized with chloral hydrate and placed in Stereotaxic frame. Guide cannula (CMA/12) was placed at AP: −5.2 mm, ML: +5.0 mm relative from bregramsa and DV: −3.8 mm from the brain surface according to the atlas of Paxinos and Watson (1986). While the animal was still anesthetized, a micro dialysis probe (CMA/12, 4 mm, PC) was inserted through the guide cannula and secured in place. After surgery recovery period of 48-72 hours was maintained before subjecting the animal for study.

A day prior to study animals were transferred to home cages for acclimatization and implanted probe was perfused overnight with a modified Ringer's solution comprised of: 1.3 M CaCl2 (Sigramsa), 1.0 μM $MgCl_2$ (Sigramsa), 3.0 M KCl (Sigramsa), 147.0 μM NaCl (Sigramsa), 1.0 μM $Na_2HPO_4.7H_2O$ and 0.2 M $NaH_2PO_4.2\ H_2O$ and 0.3 μM neostigramsine bromide (Sigramsa) (pH to 7.2) at a rate of 0.2 μL/minutes set by a microinfusion pump (PicoPlus, Harward). On the day of experiment perfusion rate was changed to 1.2 μL/minutes and allowed for 3 hours stabilization. After stabilization period, four basals were collected at 20 minutes intervals before dosing. Dialysate samples were collected in glass vials using CMA/170 refrigerated fraction collector.

Vehicle or NCE (3 mg/kg or 10 mg/kg) was administered by gavages after four fractions had been collected. The perfusate was collected until 6 hours after administration.

Acetylcholine concentrations in dialysate samples were measured by LC-MS/MS (API 4000, MDS SCIEX) method. Acetylcholine is quantified in the calibration range of 0.250 to 8.004 ng/mL in dialysates.

On completion of the microdialysis experiments, the animals were sacrificed and their brains were removed and stored in a 10% formalin solution. Each brain was sliced at 50μ on a cryostat (Leica) stained and examined microscopically to confirm probe placement. Data from animals with incorrect probe placement were discarded.

Microdialysis data were expressed as percent changes (Mean±S.E.M.) of baseline that was defined as the average absolute value (in fM/10 μL) of the four samples before drug administration.

Effects of NCE (3 & 10 mg/kg) and Vehicle treatments were statistically evaluated by one-way ANOVA followed by Dunnett's multiple comparison tests. In all statistical measures, a $p<0.05$ was considered significant. The Graph Pad Prism program statistically evaluated the data.

Example 100

Food Intake Measurement

Male Wister rats (120-140 gm) obtained from N.I.N. (National Institute of Nutrition, Hyderabad, India) was used. The chronic effect of the compounds of general formula (I) on food intake in well-fed rats was then determined as follows.

The rats were housed in single home cages for 28 days. During this period, the rats were either dosed orally or ip, with a composition comprising a compound of formula (1) or a corresponding composition (vehicle) without the said compound (control group), once a day, and the rat is provided with ad libitum food and water.

On 0, 1st, 7th, 14th, 21st and 28th day the rats were left with the pre-weighed amounts of food. Food intake and weight gain were measured on a routine basis. Also a food ingestion method is disclosed in the literature (Kask et al., European Journal of Pharmacology, 414, 2001, 215-224 and Turnball et. al., Diabetes, vol 51, August, 2002, and some in-house modifications.). The respective parts of the descriptions are herein incorporated as a reference and they form part of the disclosure.

Some representative compounds have shown the statistically significant decrease in food intake, when conducted in the above manner at the doses of either 10 mg/Kg or 30 mg/Kg or both

Example 101

Object Recognition Task Model

The cognition-enhancing properties of compounds of this invention were estimated using a model of animal cognition: the object recognition task model.

Male Wister rats (230-280 grams) obtained from N.I.N. (National Institute of Nutrition, Hyderabad, India) was used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed. T1 is the total time spent exploring the familiar objects (a1+a2). T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

Some representative compounds have shown positive effects indicating the increased novel object recognition viz; increased exploration time with novel object and higher discrimination index.

| Example Number | Dose mg/kg, p.o. | Exploration time mean ± S.E.M (sec) Familiar object | Novel object | Inference |
|---|---|---|---|---|
| 1. | 10 mg/kg, p.o. | 10.10 ± 1.84 | 13.22 ± 2.00 | Active |
| 3. | 1 mg/kg | 4.53 ± 0.72 | 10.29 ± 1.54 | Active |
| 11. | 3 mg/kg, p.o. | 9.19 ± 1.44 | 14.24 ± 1.29 | Active |
| 16. | 10 mg/kg, p.o. | 8.10 ± 1.78 | 12.00 ± 1.84 | Active |
| 28. | 1 mg/kg | 6.26 ± 0.30 | 11.46 ± 1.02 | Active |
| 35. | 10 mg/kg | 9.37 ± 1.66 | 15.81 ± 2.89 | Active |

Example 102

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm² perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition boards that determined path length, swim speed and the number of entries and duration of swim time spent in each quadrant of the water maze.

| Example Number | Scopolamine Induced Reversal |
|---|---|
| 1. | ≤10 mg/kg, p.o. |
| 16. | ≤10 mg/kg, p.o. |

Example 103

Chewing/Yawning/Stretching Induction by 5-HT$_6$ Antagonists

Male Wister rats weighing 200-250 grams were used. Rats were given vehicle injections and placed in individual, transparent chambers for 1 hour each day for 2 days before the test day, to habituate them to the observation chambers and testing procedure. On the test day, rats were placed in the observation chambers immediately after drug administration and observed continuously for yawning, stretching, and chewing behaviors from 60 to 90 minutes after drug or vehicle injections. 60 minutes prior to the drug administration Physostigramsine, 0.1 mg/kg i.p, was administered to all the animals. Average number of yawns, stretches and vacuous chewing movements during the 30 minutes observation period were recorded.

Reference: (A) King M. V., Sleight A., J., Woolley M. L., and et. al., Neuropharmacology, 2004, 47, 195-204. (B) Bentey J. C., Bourson A., Boess F. G., Fone K. C. F., Marsden C. A., Petit N., Sleight A. J., British Journal of Pharmacology, 1999, 126 (7), 1537-1542).

Example 104

Passive Avoidance

Animals were trained in a single-trial, step through, and light-dark passive avoidance paradigrams. The training apparatus consisted of a chamber 300 mm in length, 260 mm wide, and 270 mm in height, constructed to established designs. The front and top were transparent, allowing the experimenter to observe the behaviour of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 seconds across the 16 bars. A resistance range of 40-60 micro ohms was calculated for a control group of rats and the apparatus was calibrated accordingly. An electronic circuit detecting the resistance of the animal ensured an accurate current delivery by automatic variation of the voltage with change in resistance.

Experimental Procedure

This was carried out as described previously. Adult male Wister rats weighing 200-230 grams were used. Animals were brought to the laboratory 1 hour before the experiment. On the day of training, animals were placed facing the rear of the light compartment of the apparatus. The timer was started once the animal has completely turned to face the front of the chamber. Latency to enter the dark chamber was recorded (usually <20 seconds) and having completely entered the dark compartment an inescapable foot shock of 0.75 mA for 3 seconds was administered to the animal. Animals were then returned to their home cages. Between each training session, both compartments of the chamber were cleaned to remove any confounding olfactory cues. Recall of this inhibitory stimulus was evaluated 24 hours, 72 hours and on $7^{th}$ day post-training by returning the animal into the light chamber and recording their latency to enter the dark chamber, a criterion time of 300 seconds was employed.

Reference: (A) Callahan P. M., Rowe N. B., Tehim A., Abst. 776.19.2004, Society for neuroscience, 2004. (B) Fox G. B., Connell A. W. U., Murphy K. J., Regan C. M., Journal of Neurochemistry, 1995, 65, 6, 2796-2799.

We claim:
1. A compound which is selected from the group consisting of:
   N-[2-Methyl-5-(6-chloro-1H-indole-3-yl sulfonyl)phenyl]-N-(1-methyl piperidin-4-yl)amine;
   N-(1-Methyl piperidin-4-yl)-N-[3-(6-chloro-1H-indole-3-yl sulfonyl)phenyl]amine hydrochloride;
   N-(1-Methyl piperidin-4-yl)-N-[3-(5-fluoro-1H-indole-3-yl sulfonyl)phenyl]amine hydrochloride;
   N-(1-Methyl piperidin-4-yl)-N-[2-chloro-5-(6-chloro-1H-indole-3-yl sulfonyl)phenyl]amine hydrochloride;
   N-(1-Methyl piperidin-4-yl)-N-[2-methoxy-5-(1H-Indole-3-yl sulfonyl)phenyl]amine;
   N-(1-Methyl piperidin-4-yl)-N-[2-methoxy-5-(5-methoxy-1H-Indole-3-yl sulfonyl)phenyl]amine;
   N-(Piperidin-4-yl)-N-[2-methoxy-5-(5-methoxy-1H-Indole-3-yl sulfonyl)phenyl]amine;
   N-(Piperidin-4-yl)-N-[2-methoxy-5-(6-chloro-1H-Indole-3-yl sulfonyl)phenyl]amine; and
   N-(1-Methyl piperidin-4-yl)-N-[2-methoxy-5-(6-chloro-1H-Indole-3-yl sulfonyl)phenyl]amine.

2. A pharmaceutical composition comprising a pharmaceutically acceptable carrier, diluent, excipient or solvate along with a therapeutically effective amount of a compound according to claim 1.

3. A method for the treatment of Alzheimer's disease or schizophrenia, in a patient in need thereof, which comprises the step of providing to said patient a therapeutically effective amount of the compound of claim 1.

4. The compound of claim 1, wherein the compound is N-[2-Methyl-5-(6-chloro-1H-indole-3-yl sulfonyl)phenyl]-N-(1-methyl piperidin-4-yl)amine.

5. The compound of claim 1, wherein the compound is N-(1-Methyl piperidin-4-yl)-N-[3-(6-chloro-1H-indole-3-yl sulfonyl)phenyl]amine hydrochloride.

6. The compound of claim 1, wherein the compound is N-(1-Methyl piperidin-4-yl)-N-[3-(5-fluoro-1H-indole-3-yl sulfonyl)phenyl]amine hydrochloride.

7. The compound of claim 1, wherein the compound is N-(1-Methyl piperidin-4-yl)-N-[2-chloro-5-(6-chloro-1H-indole-3-yl sulfonyl)phenyl]amine hydrochloride.

8. The compound of claim 1, wherein the compound is N-(1-Methyl piperidin-4-yl)-N-[2-methoxy-5-(1H-Indole-3-yl sulfonyl)phenyl]amine.

9. The compound of claim 1, wherein the compound is N-(1-Methyl piperidin-4-yl)-N-[2-methoxy-5-(5-methoxy-1H-Indole-3-yl sulfonyl)phenyl]amine.

10. The compound of claim 1, wherein the compound is N-(Piperidin-4-yl)-N-[2-methoxy-5-(5-methoxy-1H-Indole-3-yl sulfonyl)phenyl]amine.

11. The compound of claim 1, wherein the compound is N-(Piperidin-4-yl)-N-[2-methoxy-5-(6-chloro-1H-Indole-3-yl sulfonyl)phenyl]amine.

12. The compound of claim 1, wherein the compound is N-(1-Methyl piperidin-4-yl)-N-[2-methoxy-5-(6-chloro-1H-Indole-3-yl sulfonyl)phenyl]amine.

* * * * *